US012753398B2

(12) United States Patent
Risacher

(10) Patent No.: US 12,753,398 B2
(45) Date of Patent: Oct. 6, 2026

(54) CRISPR-MEDIATED DIRECTED CODON RE-WRITE

(71) Applicant: LIMAGRAIN EUROPE, Saint-Beauzire (FR)

(72) Inventor: Thierry Risacher, Clermont-Ferrand (FR)

(73) Assignee: LIMAGRAIN EUROPE, Saint-Beauzire (FR)

( * ) Notice: Subject to any disclaimer, the term of this patent is extended or adjusted under 35 U.S.C. 154(b) by 779 days.

(21) Appl. No.: 18/027,530

(22) PCT Filed: Oct. 1, 2021

(86) PCT No.: PCT/EP2021/077206
§ 371 (c)(1),
(2) Date: Mar. 21, 2023

(87) PCT Pub. No.: WO2022/069756
PCT Pub. Date: Apr. 7, 2022

(65) Prior Publication Data

US 2023/0348874 A1 Nov. 2, 2023

(30) Foreign Application Priority Data

Oct. 2, 2020 (EP) ..................................... 20306150

(51) Int. Cl.
*C12N 9/22* (2006.01)
*C12N 15/10* (2006.01)
*C12N 15/82* (2006.01)

(52) U.S. Cl.
CPC ............. *C12N 9/22* (2013.01); *C12N 15/102* (2013.01); *C12N 15/8213* (2013.01); *C12N 2310/20* (2017.05)

(58) Field of Classification Search
None
See application file for complete search history.

(56) References Cited

U.S. PATENT DOCUMENTS

| | | | | |
|---|---|---|---|---|
| 2018/0273960 | A1* | 9/2018 | Cigan | A01H 4/008 |
| 2020/0040329 | A1 | 2/2020 | Gifford et al. | |
| 2021/0087573 | A1* | 3/2021 | Gasior | C12N 15/8213 |
| 2023/0287389 | A1 | 9/2023 | Jiang et al. | |

FOREIGN PATENT DOCUMENTS

| | | | |
|---|---|---|---|
| WO | 2016183438 | A1 | 11/2016 |
| WO | 2017070029 | A1 | 4/2017 |
| WO | 2017070032 | A1 | 4/2017 |
| WO | 2018092072 | A1 | 5/2018 |
| WO | 2019048618 | A1 | 3/2019 |
| WO | 2019217358 | A1 | 11/2019 |

OTHER PUBLICATIONS

Brinkman et al., Kinetics and Fidelity of the Repair of Cas9-Induced Double-Strand DNA Breaks. Molecular Cell (2018), 70: 801-813 (Year: 2018).*
International Search Report and Written Opinion issued on Jan. 28, 2022 for corresponding PCT Application No. PCT/EP2021/077206.
Xu Wen et al.: “Versatile Nucleotides Substitution in Plant Using an Improved Prime Editing System”, Molecular Plant, vol. 13, No. 5, 2020, pp. 675-678 XP055880777.
Lin Qiupeng et al.: “Prime genome editing in rice and wheat”, Nature Biotechnology, vol. 38, No. 5, 2020, pp. 582-585 XP037113496.
S. D. Perli et al.: “Continuous genetic recording with self-targeting CRISPR-Cas in human cells”, Science, vol. 353, No. 6304, 2016, pp. aag0511-aag0511 XP055309113.

* cited by examiner

*Primary Examiner* — Catherine Konopka
(74) *Attorney, Agent, or Firm* — POLSINELLI PC

(57) ABSTRACT

The invention relates to methods for introducing mutation within genes, which use the errors in the reparation machinery of the cell, and introduction of deletions and/or insertions when repairing a cleavage made by an endonuclease, in particular using the CRISPR system.

17 Claims, 4 Drawing Sheets

Specification includes a Sequence Listing.

```
                    Asp                       Upper case: Target codon
5' gagcattctgactctgatGATgccaggagacgca 3'     Underlined : PAM
        attctgactctgatgatgcc                  ZmHRC_Asp94_for_spacer (SEQ ID NO: 3)
```

Fig. 1

```
Wild type ZmHRC   GAGCATTCTGACTCTGATGAT-GCCAGGAGA
           ins1   GAGCATTCTGACTCTGATGATTGCCAGGAGA
           del1   GAGCATTCTGACTCTGATGA--GCCAGGAGA
           del3   GAGCATTCTGACTCTGAT----GCCAGGAGA
           del2   GAGCATTCTGACTCTGATG---GCCAGGAGA
           del6   GAGCATTCTGACTCT-------GCCAGGAGA
```

Fig. 2

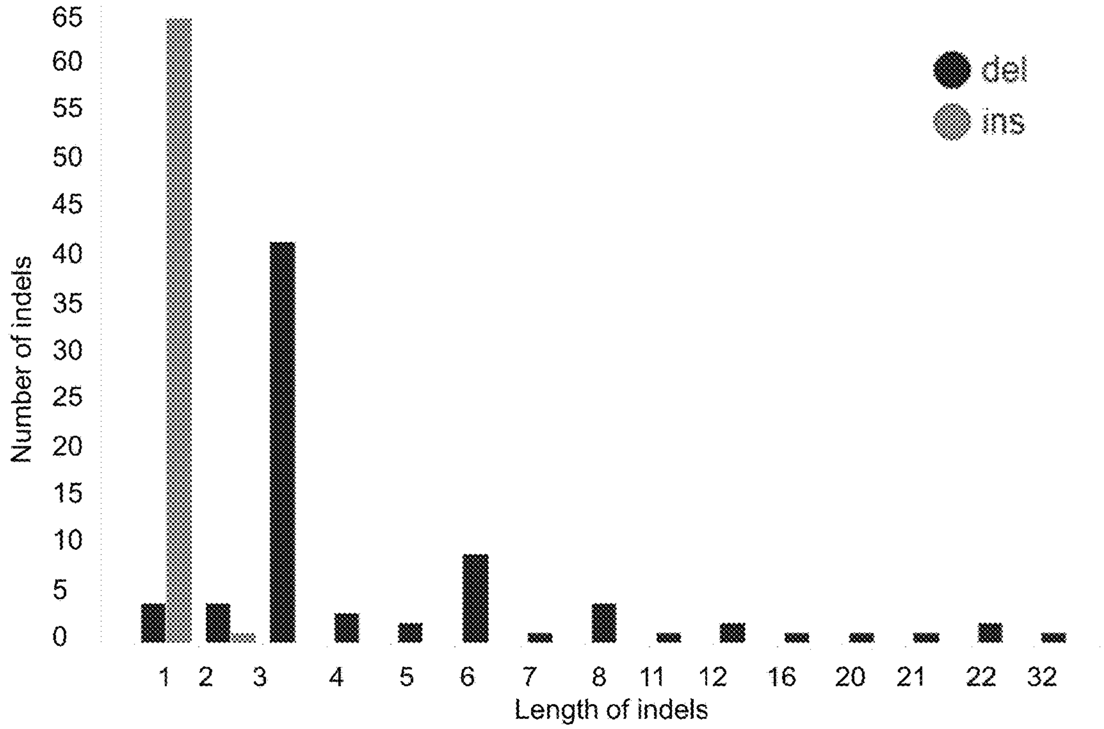

Fig. 3

(Asp)

5' gagcattctgactctgat----gccaggagacgca 3' agcattctgactctgat----gcc

Upper case: Target codon

Underlined : PAM

ZmHRC_Asp94-del3_for_spacer (SEQ ID NO: 12)

Fig. 4

(Asp)

5' gagcattctgactctgatT--gccaggagacgca 3' gcattctgactctgatt--gcc

Upper case: Target codon

Underlined : PAM

ZmHRC_Asp94-del3insT_for_spacer (SEQ ID NO: 15)

Fig. 5

(Asp)

5' gagcattctgactctgatTT-gccaggagacgca 3' cattctgactctgattt-gcc

Upper case: Target codon

Underlined : PAM

ZmHRC_Asp94-del3insTT_for_spacer (SEQ ID NO: 18)

Fig. 6

Phe

5' gagcattctgactctgatTTTgccaggagacgca 3'

Upper case: Target codon

Underlined : PAM

Fig. 7

Val

5'cacctacGTCgacacccccggcgagt

3'gtggatgcagctgtgggggccgctca tgcagctgtgggggccg

Upper case: Target codon

Underlined : PAM

TaLox1_Val286_rev_spacer (Wang et al, 2018) SEQ ID NO : 21

Fig. 8

| | |
|---|---|
| Wild type TaLox1 | CACCTACG--TCGACACCACCCCCGGCGAGT |
| ins1 | CACCTACGATCGACACCACCCCCGGCGAGT |
| del3 | CACCTACG--------ACACCACCCCCGGCGAGT |
| del2 | CACCTACG-----GACACCACCCCCGGCGAGT |
| del5 | CACCTACG----------ACCACCCCCGGCGAGT |
| del1 | CACCTACG---CGACACCACCCCCGGCGAGT |

Fig. 9

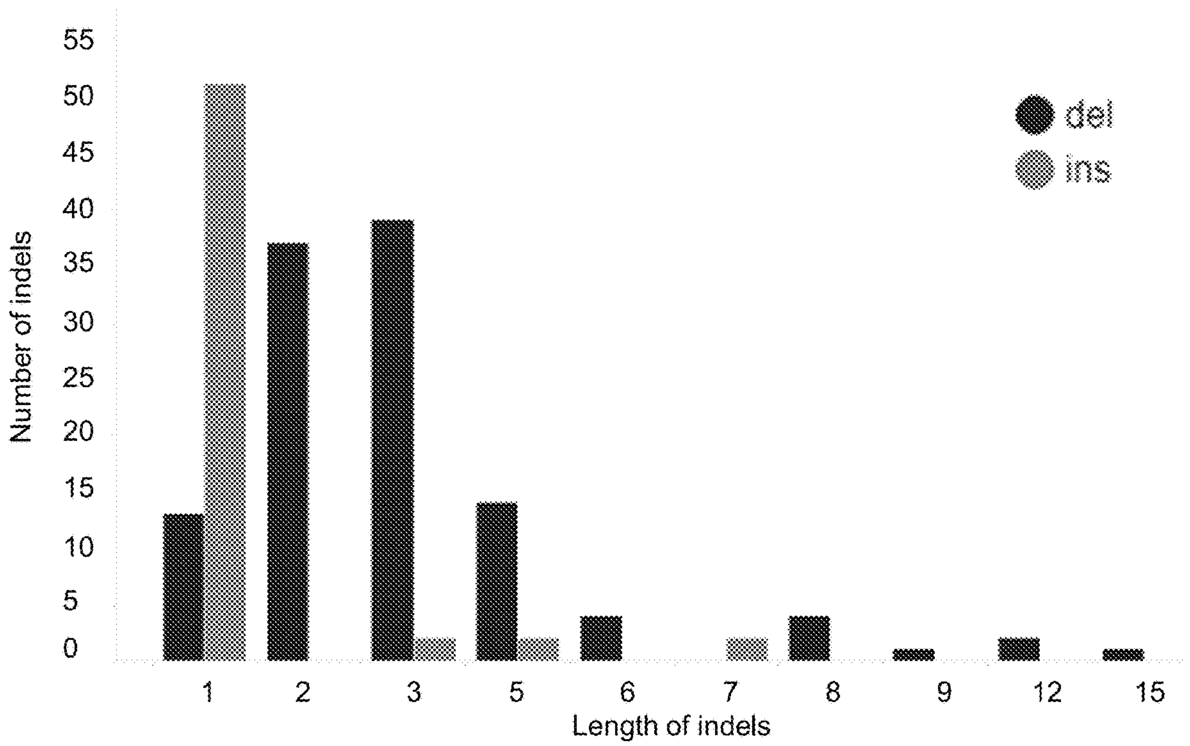

Fig. 10

```
         Val-del2
5'cacctacG--gacacccccggcgagt        Upper case: Target codon ; Dashes: deletion
3'gtggatgc--ctgtgggggccgctca        Underlined : PAM
     tgc--ctgtgggggccgct            TaLox1_Val286-del2_rev_spacer SEQ ID NO : 27
```

Fig. 11

```
         Val-del2insA
5'cacctacG-Agacacccccggcgagt        Upper case: Target codon ; Dashes: deletion
3'gtggatgc-tctgtgggggccgctca        Underlined : PAM
     tgc-tctgtgggggccgc             TaLox1_Val286-del2insA_rev_spacer SEQ ID NO : 30
```

Fig. 12

```
         Glu
5'cacctacGAAgacacccccggcgagt        Upper case: Target codon
3'gtggatgcttctgtgggggccgctca        Underlined : PAM
```

Fig. 13

Ser
atgtgttgcctatgatccctAGTggtggggcttt
ttgcctatgatccctagtgg

Upper case: Target codon
Underlined : PAM
ZmALS2_Ser621_for_spacer SEQ ID NO: 35

Fig. 14

Ser
atgtgttgcctatgatccctA-Tggtggggcttt
gttgcctatgatccct a-tgg

Upper case: Target codon
Underlined : PAM ; Dashes: deletion
ZmALS2_Ser621del1_for_spacer SEQ ID NO: 38

Fig. 15

Asn
atgtgttgcctatgatccctAATggtggggcttt

Upper case: Target codon
Underlined : PAM

Fig. 16

CRISPR-MEDIATED DIRECTED CODON RE-WRITE

CROSS-REFERENCE TO RELATED APPLICATIONS

This application is a national stage application (under 35 U.S.C. § 371) of PCT/EP2021/077206, filed Oct. 1, 2021, which claims benefit of European Application No. 20306150.2, filed Oct. 2, 2020, which are incorporated herein by reference in their entireties.

The invention relates to methods for introducing mutation within genes (gene editing), which use the reparation machinery of the cell and in particular gene editing by the CRISPR system.

Gene editing (GE) by the CRISPR/Cas system is a tool widely used worldwide to edit prokaryotic and eukaryotic genomes. (Jinek, M. et al. Science 337, 816-821 2012, Cong, L. et al. Science 339, 819-823 2013) Three types of editing can be obtained after a Double Stranded-Break (DSB) made by a CRISPR/Cas system. SDN1 editing means that the repair of the DNA strands is made by one pathway of the cellular DNA repair machinery: the Non-Homologous End Joining pathway (NHEJ). The repair can result in small insertions or deletions (indels) at the cleavage site.

SDN2 is an editing where the repair is made by the insertion of a sequence by homologous recombination (HR) using a template. The insertion is usually identical to the target sequence but comprises a desired correction.

SDN3 is also an editing where the repair is made by HR but the insertion is a new genetic material.

Base editing (BE) has become an important tool in genome engineering. Currently, tools exist to target Cytidine residues and more recently Adenine residues (Cytidine Base Editors and Adenine Base Editors) (Kim (2018), Rees and Liu (2018)). These Base Editors consist of a cytidine deaminase or an adenine deaminase linked to a DNA targeting system allowing the deaminase activity to be directed to a specific DNA region. Deaminase activity for the cytidine deaminase converts in majority a C residue to a T. However, depending on the enzyme and BE construction used, other bases can be introduced. The Adenine BE is more specific, converting an A residue only to a G residue.

The applicant has developed a method that is both an alternative and an improvement to CRISPR/Cas9 Base Editing and to small SDN2 by using iterative Cas9 gene editing to modify and direct the change of several bases in one or two codons without a Base-editor.

The technique is able to direct the editing of one or two codons in a nucleic acid sequence and can generate a modification of one or two specific amino acids in the resulting protein sequence. The Directed Codon Re-Write is achieved at the position cleaved by the CRISPR Cas endonuclease which makes it very versatile when used for example with a broad PAM variant such as xCas9. As it doesn't require a template sequence for SDN2 and homologous recombination, it is expected to be more efficient than oligo-based SDN2.

The method herein disclosed is alternatively called Codon replacement or codon re-write or directed codon re-write.

A codon is a series of three successive nucleotides in a nucleic acid sequence encoding an amino acid or a stop signal during protein synthesis.

Nucleotide and base are used alternatively to designate the basic components of a nucleic acid sequence: Adenine (A), Cytosine (C), Guanine (G) and Thymine (T).

A PAM is a Protospacer Adjacent Motif, which is a DNA sequence (usually 2-6-base pair) in the DNA sequence targeted by the endonuclease in the CRISPR system. The motif is essential for the recognition of the targeted region by the CRISPR endonuclease. A PAM sequence is specific of a CRISPR endonuclease. The PAM sequence of a CRISPR endonuclease determines the possible area that can be targeted in the targeted genome.

The wild type sequence, or original sequence, or initial sequence, is the target sequence before performance of the method, and thus before introduction of mutations.

The method of the invention is based on the gene editing CRISPR technology and the error-prone repairs of the NHEJ cellular DNA repair machinery. The NHEJ pathway is the predominant mechanism for DSB repairs. This pathway joins two broken DNA ends (Lieber 2010). The NHEJ pathway will either repair the DNA and restore the integrity of the original DNA sequence or introduce errors in the repaired DNA, for example small deletions or insertions at the junction.

The codon re-write machinery requires a CRISPR endonuclease generating blunt ends and at least 2 guide RNA (gRNA) used successively or concomitantly.

The method of the invention allows to introduce specific modifications in a targeted organism.

The method can be applied to eukaryotic cells (animal, fungal or plant cells; preferably plants cells; more preferably corn, wheat, rice, rapeseed, sunflower, barley, rye, soybean, cotton, sorghum, beetroot) or prokaryotic cells.

In more details, the invention thus relates to a method for introducing a specific mutation at a specified position of a target gene, comprising a) Introducing, in cells of a plurality of cells,
  - an endonuclease protein,
  - a first guide RNA (primary guide) that recognizes a targeted position in the target gene,
  - a second guide RNA (secondary guide) that recognizes a modified targeted position in the target gene, wherein the modification consists in at least one nucleotide deletion, b) optionally screening the plurality of cells to isolate the cell in which the specific mutation has been introduced without introducing a frameshift.

Consequently, the method allows obtaining a cell of an organism in which the specific mutation has been introduced at the specified position (or location) in the target gene. The target gene codes for a given protein. The method is performed when one wishes to modify one or two codons of the protein, so that one or two amino acids of the protein sequence are modified.

The first guide RNA will trigger cleavage of the double-strand DNA at a given position in the target gene. Said position depends on both the location of the PAM close to the given position (it is reminded that the protospacer adjacent motif (PAM) is a short DNA sequence usually 2-6 base pairs in length that follows the DNA region targeted for cleavage by the CRISPR system), and of the endonuclease used.

After cleavage of the DNA strand, the cell DNA repair machinery starts working to repair the cleaved DNA. During this process, some errors can happen, so that usually one, two or three nucleotides are deleted in the repaired DNA sequence at the location of the cleavage. Larger deletions can also occur but are not desired for the codon-rewrite method. Alternatively, some nucleotides insertions are also possible during the process of DNA repair by the cell machinery.

The invention thus uses the fact that the first guide RNA directs the nuclease to cleave the target gene at the targeted position, and that small deletions from 1 to 3 nucleotides are introduced by reparation at the cleavage site in some cells. Consequently, some cells contain a modified targeted position, with one, two or three nucleotides missing at this location.

The second guide RNA directs the nuclease to cleave the target gene at the modified targeted position. Upon this second cleavage, it is intended to have insertion of a desired nucleotide during reparation at the cleavage site, the desired nucleotide being different from the original nucleotide at this position, thereby introducing by reparation of the target gene the specific mutation at the specified position of the target gene.

This embodiment as explained when only two guides RNA are used (substitution of one nucleotide by successive deletion and insertion) can be broadened, as disclosed below, for substituting more than one nucleotide, using more guides RNA, to take advantage of the fact that the repair can introduce deletion of more than one nucleotide after cleavage directed by the first guide RNA.

In one embodiment, the plurality of cells is a tissue of the organism (a part of the organism which is typically self-contained and has a specific function). In another embodiment, the plurality of cells is a tissue. In another embodiment, the plurality of cells is a suspension of cells of the organism. In yet another embodiment, the plurality of cells are cells that have been made adherent to the culture recipient.

In a preferred embodiment, the organism is a plant. In particular, the plant is a monocotyledon, preferably a cereal. As monocotyledonous plants, one can cite cereals like rice, wheat, barley, sorghum, oat, maize but also sugarcane. The method can advantageously be performed with wheat or maize cells. In another embodiment, the plant is a dicotyledon. Among dicotyledonous plants, one can cite soybean, cotton, tomato, beet, sunflower, or rapeseed.

In a preferred embodiment, the plurality of plant cells are microspores, ovules, protoplasts, zygotes. In a specific embodiment, the cells are plated for biolistics transformation.

In a preferred embodiment the plant tissue is an embryo, meristems like apical meristem, leaves, roots, stems, hypocotyls.

When the method is performed on plant cells, one can use the totipotency property of such plant cells, which makes it possible to regenerate a whole plant from a given cell (for instance after growing the cell and forming a callus from the cultured cells), and hence a plant in which the mutations have been introduced at the specified target locus.

When the method is performed on plant germinal cells (pollen, ovule), the plant germinal cell can be used to fertilize another germinal cell, and to generate a plant so as to introduce the mutation in the resulting plant. In another embodiment, a double haploid is generated, and a plant is regenerated.

In one embodiment, the mutation is the replacement of one nucleotide in the target gene. In this embodiment, one can make use of only two guides RNA. The first guide is intended to direct the first cleavage. it is reminded that the targeting specificity of CRISPR-Cas9 is determined by a 20-nt sequence at the 5' end of the gRNA. After base pairing of the gRNA to the target, Cas9 mediates the double strand break about 3-4 nucleotides upstream of PAM at the desired target sequence The second guide RNA is designed to direct the cleavage to the initial sequence at the locus, minus one nucleotide at the site where the cleavage has occurred with the first gRNA. Hence, the second gRNA will only recognize and direct a cleavage for the cells in which repair after the first cleavage was not proper and one deletion was introduced during this repair step. The endonuclease thus cleaves again the double stranded site at the target site with the deletion.

Repair will then occur again, and a random nucleotide may be inserted at the cleavage site. It is thus possible to screen for identifying the cells in which the desired nucleotide has been inserted, in substitution to the original nucleotide, thereby obtaining a cell in which the mutation has been introduced.

In another embodiment, a third guide RNA (ternary guide) is introduced in the cells with the endonuclease protein and the first and second guide RNAs, and (i) wherein the second guide RNA is designed so as to recognize a modified targeted position wherein modification consists in a deletion of two desired nucleotides at the specified position in the target gene after the cleavage with the first guide RNA and wherein the repair after the cleavage with the second guide RNA inserts a first desired nucleotide at the modified targeted position (ii) wherein the third guide RNA is designed so as to recognize the modified targeted position with the insertion obtained in (i), and wherein the repair after the cleavage with the third guide RNA inserts a second desired nucleotide at the modified targeted position thereby resulting in a mutated target gene (in which two desired nucleotides have replaced two original nucleotides, with at least one nucleotide being different from the original nucleotide or the two desired nucleotides being different from the two original nucleotides).

In this embodiment, three guides RNA are used and the method takes advantage of the fact that a deletion of two desired nucleotides may be introduced when the cleavage directed by the first gRNA is repaired, thereby leading to a modified sequence.

In this embodiment, the second guide RNA recognizes the modified sequence (original sequence minus the deletion of two desired nucleotides at the first cleavage site) and is able to direct the endonuclease to perform a cleavage in the cells having this modified sequence. After the cleavage, the repair mechanism will close the double strand, and one random nucleotide may be inserted, leading to secondary modified sequences.

The third RNA guide is specific to the secondary modified sequence in which a first desired nucleotide has been inserted. This first desired nucleotide is different from the original nucleotide that was at this location. The third gRNA directs the endonuclease to cleave the secondary modified sequence.

A second desired nucleotide may be inserted at the repair site. It is thus possible to screen for identifying the cells in which the second desired nucleotide has been inserted.

It is to be noted that the second desired nucleotide, which is inserted after cleavage directed by the third gRNA, may be identical to the original nucleotide that was present at the same location in the original (non-mutated sequence). This may occur when one wishes to modify only the first desired nucleotide in the two nucleotide-deletion.

In this embodiment, one or two codons of the original target gene can be modified if the specific mutation overlaps two codons.

In another embodiment, four guides RNA are used: the first gRNA directs a cleavage in the original sequence, the second gRNA is specific for the original sequence with a deletion of three desired nucleotides at the cleavage site, the third gRNA is specific for the original sequence with a deletion of three desired nucleotides and one insertion of a first desired nucleotide different from the original nucleotide, and the fourth gRNA is specific for the original sequence in which a deletion of three desired nucleotides was made after the first cleavage and after which two desired nucleotides have been inserted successively during repairs (after the cleavages with the second and third gRNA).

In short, the first gRNA directs a cleavage at the predetermined site. Repair may introduce a deletion of three desired nucleotides, thereby leading to a first modified sequence.

The second gRNA is specific to the first modified sequence and directs the cleavage by the endonuclease. Upon repair, insertion of one random nucleotide can arise, thereby leading to a second modified sequence.

The third gRNA is specific for the second modified sequence in which a first desired nucleotide (different from the original one) has been inserted. It directs an endonuclease cleavage and repair, upon which one random nucleotide may be inserted (downstream the first desired nucleotide), leading to a third modified sequence.

The fourth gRNA (quaternary guide) is specific for the third modified sequence, in which a second desired nucleotide has been inserted. It directs an endonuclease cleavage and repair, upon which one random nucleotide may be inserted (downstream the second desired nucleotide), leading to a fourth modified sequence.

Upon screening of the cells having fourth modified sequences, it is possible to identify the cells for which a third desired nucleotide has been inserted downstream the second desired nucleotide.

It is to be noted that, although the first desired nucleotide is different from the original nucleotide at the same location, one or the other two desired nucleotides may be identical to the ones that were in the original sequence. In one embodiment, the first desired nucleotide is different, but the two last reintroduced nucleotides are identical to the ones in the original sequence. In another embodiment, the two first desired nucleotides are different but the last one reintroduced is identical to the one in the original sequence. In another embodiment, the three desired nucleotides are different than the ones in the original sequence.

In this embodiment, a fourth guide RNA is introduced in the cells with the endonuclease protein and the first, second and third guide RNAs, and (i) wherein the second guide RNA is designed so as to recognize a modified targeted position wherein the modification consists in a deletion of three nucleotides at the specified position in the target gene after the cleavage with the first guide RNA and wherein the repair after the cleavage with the second guide RNA inserts a first desired nucleotide at the modified targeted position (ii) wherein the third guide RNA is designed so as to recognize the modified targeted position obtained after the insertion obtained in (i), and wherein the repair after the cleavage with the third guide RNA inserts a second desired nucleotide at the modified targeted position (iii) wherein the fourth guide RNA is designed so as to recognize the modified targeted position with the insertion obtained in (ii), and wherein the repair after the cleavage with the fourth guide RNA inserts a third desired nucleotide at the modified targeted position thereby resulting in cells in which the target gene is mutated, (in which three desired nucleotides have replaced three original nucleotides, with at least one nucleotide being different from the corresponding original nucleotide, or two nucleotides being different from the corresponding original nucleotides, or the three nucleotides being different from the original nucleotides).

The endonuclease, and the guides RNA can be delivered into plants as ribonucleoprotein complexes (RNP), or using vectors comprising genetic constructs encoding the different elements.

The delivery methods are known by the skilled person. For example, mention may be made of electroporation, biolistics, virus-mediated transformation, *Agrobacterium* mediated plant transformation (Ishida et al., 1996)

Vectors comprising genetic constructs encoding the different elements may be plasmids. The nucleic acids encoding the endonuclease and the gRNA are placed under the control of promoters. Promoters of the invention comprise constitutive promoters like the ZmUbi promoter, the TaU6 promoter, the maize U6 promoter, the maize U3 promoter, the rice U3 promoter and the rice U6 promoter.

Optionally, the vector can comprise a selectable marker like bar, nptll, hygromycin and or a visual marker (GFP, luciferase, GUS).

The RNP complexes comprising the endonuclease and the gRNAs are produced and assembled in vitro and delivered in the target cells (bombardment, electroporation, PEG transformation).

As indicated above, it is preferred when the mutation induces a change of an amino acid in the protein coded by the gene. In another embodiment, the mutation results in a change in two consecutive amino acids of the protein (when the ability of repair to introduce two or three deletions is used, when the specified position comprises two or three nucleotides of two codons of a gene encoding a protein, and wherein the mutation includes the mutation of at least two of these nucleotides, thereby triggering a change of two amino acids in the protein). In another embodiment, the mutation creates a stop codon in the coding sequence, thereby leading to a truncated protein. In another embodiment, the mutation is introduced in a regulatory region of the gene, for instance in the gene's promoter so as to reduce or increase expression of the gene.

In the preferred embodiment, the cells are cultured in vitro to increase their number. In another embodiment, when the organism is a plant, the cells in which the target gene has been mutated are recovered, and a whole plant/plantlet is regenerated (in particular, the cells are allowed to form a callus and the plant is regenerated from the callus). A sample of each regenerated plant/plantlet is taken for analysis. The whole DNA is extracted from each sample and sequenced to detect the presence of the specific mutation. Alternatively, primers specific of the target region in the target genes are used to amplify the target region. The target region is sequenced to detect the presence of the specific mutation.

Screening may be performed on plants regenerated from the plurality of cells. One should note that the regenerated plants are generally chimeras plants (as they contain various mutated cells (several mutation events can be present in view of the iterative method herein disclosed) as well as non-mutated cells. One way of obtaining plants with the mutation in all cells would be to screen the regenerated plants to select the ones in which it is most likely that germinal cells would contain the specific mutation.

One way to perform this screening would be to use a sample (somatic tissue) of the regenerated plant, as described above and to perform a quantitative analysis of the DNA bearing the mutation. The higher the mutation rate in somatic cells, the more likely the mutation occurred early in the cell divisions and regeneration and the higher the chance that germ cells are also mutated and thus that the mutation is transmissible. Consequently, by screening multiple regenerated plants using similar samples from each plant (for instance a circle taken from a leaf by a punch), it is possible, by quantifying the amount of mutated DNA to evaluate the quantity of cells that contain the specific mutation and to select the plants from which these cells were harvested. For instance, it is possible to rank the plants according to the amount of mutation in the sample (thus the importance to take similar samples for mutation DNA analysis), and select the first decile (the 10% of plants that have the highest amount of mutations in the analyzed DNA) for further processing. In another embodiment, the 5% of plants, or the 2% of plants, or the 1% of plants having the highest amount of mutations in the analyzed DNA are selected.

Such selected plants can be used for further crosses with other plants. A percentage of the next generation plants will be heterozygous for the specific mutation.

Another method could be not to analyze the regenerated plants, but to cross these plants and to screen for the presence of the specific mutation in the progeny.

If the specific mutation introduces a herbicide tolerance in plants, the cells are selected on a selective medium comprising said herbicide.

In another embodiment, a plant comprising at least one cell containing a mutation at the specified position of the target gene is regenerated from the cell population.

The endonuclease that is used can be selected from endonucleases known in the art. It is preferably a CRISPR Cas endonuclease, most preferably a Class 2 type II (Cas9) endonuclease. One can use a Cas9 originating from any known host, such as *Streptococcus pyogenes* (SpCas9) *Staphylococcus aureus* (SaCas9), *Campylobacter jejuni* (CjCas9), *Streptococcus thermophilus* (St1Cas9), *Neisseria meningitidis* (MnCas9), *Francisella novicida* (FnCas9), E1369R/E1449H/R1556A triple mutant of *Francisella novicida* (RHA FnCas9), improved Cas9 (xCas9 described by Hu et al, Nature. 2018 Apr. 5; 556(7699):57-63), or Cas9-NG (Ren et al, Molecular Plants, 12 (7), 2019, 1015-1026). The endonuclease to be used in the methods herein disclosed must generate blunt ends when cleaving the target sequence.

The invention also relates to a method for producing a plant comprising at least one cell containing a mutation at a specified position of a target gene, comprising performing the method for introducing a mutation in the target gene, as disclosed above, and regenerating the plant from the cells obtained after performance of the method. This method may also include a step of selecting a plant from the plurality of plants regenerated from the plurality of cells, according to the method indicated above.

The invention also relates to a method for designing guides necessary for the introduction of a specific mutation at a specified position of a target gene of a cell of an organism, comprising:

identifying the nucleotides/bases that need to be replaced to modify the specified position by determining the nucleotide(s) that need to be deleted and the desired nucleotide(s) to be inserted to replace the deleted nucleotide(s) at the specified position Identifying a PAM near the specified position in the target gene, wherein the PAM is selected according to the endonuclease used for the editing Designing the first guide to have the endonuclease cleave the double stranded DNA at the specified position in the wild-type sequence designing the second guide that is specific of the deletion of the nucleotide(s) obtained after the cleavage by the endonuclease triggered by the first guide if two nucleotides are to be deleted from the wild type sequence, designing a third guide wherein the third guide triggers cleavage of the repaired sequence expected after action of the second guide leading to introduction of a desired nucleotide, and if three nucleotides are to be deleted from the wild type sequence, designing a fourth guide wherein the fourth guide triggers cleavage of the repaired sequence expected after action of the third guide leading to introduction of a desired nucleotide.

The method is thus a directed iterative enrichment in the random mutations obtained from the non-homologous end joining repair following CRISPR application to obtain the desired mutation using specifically designed guides depending on the intended modification, to direct codon re-writing.

The first guide (primary guide) and the endonuclease of the invention are able to target the native (wild-type) sequence inducing a break at the desired nucleotide(s) to re-write. A reasonably high frequency of small deletions from 1 to 3 nucleotides or insertions of 1 nucleotide will appear in some cells.

Introduced simultaneously or subsequently, a second guide (secondary guide) that recognizes the native sequence having the desired deletion (1 to 3 nucleotides) is delivered to the cells. In the case of the occurrence of the desired deletion, the mutated sequence will be cut again by the endonuclease thanks to the secondary guide. This time taking advantage of the high frequency of insertions, a fraction of cells will insert a new nucleotide.

If the re-write intended is 1 nucleotide, the cells/plants are analysed and edited plants with the desired nucleotide coding for the appropriate codon are selected.

If the re-write intended is 2 or 3 nucleotides (based on a 2 or 3 nucleotides deletion event), a third (tertiary guide) and a fourth (quaternary) guides specific to the deletion and each successive insertion(s) of the desired nucleotide are also co-introduced and functioning in a reiterative manner. The cells/plants are analysed and edited plants with the desired nucleotide coding for the appropriate codon are selected.

If a Re-write of 1 nucleotide in a codon is targeted, the codon re-write machinery comprises at least 2 guide RNAs. The codon re-write will be a partial codon-rewrite.

If a Re-write of 2 nucleotides in a codon is targeted, the codon re-write machinery comprises at least three guide RNAs. The codon re-write will be a partial codon-rewrite.

If a Re-write of 3 nucleotides in a codon is targeted, the codon re-write machinery comprises at least four guide RNAs. The codon re-write will be a complete codon-rewrite.

Herein are disclosed several steps:

Step 1=Identify the targeted nucleotide codon in the targeted nucleic acid sequence of interest in a targeted organism and identify the nucleotides/bases that need to be replaced to modify said codon by successive deletion/addition of nucleotides at each cleavage event. At the end, the same number of bases are deleted and added in the sequence so that there is no frameshift within the targeted nucleic acid of interest.

The modification of the targeted codon will induce a modification at the protein level with an amino acid modification within the sequence of the protein encoded by the targeted nucleic acid of interest compared to the wild-type protein. In some embodiments the mutation introduces a STOP codon in the gene sequence.

This amino acid modification in the protein brings a specific trait to the targeted organism.

Traits of interest in plants are for example: yield improvement, improvement of the uptake of nutrients, improvement of the plant architecture, improvement of tolerance to abiotic stress (heat, cold, drought, salinity, osmotic stress . . . ), improvement of organoleptic properties, tolerance to resistance to biotic stress (insects, nematodes, fungi, bacteria, viruses . . . ) tolerance to herbicides/antibiotics, improvement of seed oil content, improvement of seed protein content.

Step 2=PAM identification near the targeted nucleotide codon in the targeted nucleic acid sequence of interest depending on the endonuclease used for the editing The skilled person knows the PAM specificity of different endonucleases.

Endonucleases of the invention are CRISPR endonucleases generating blunt ends, typically class 2 Type II CRISPR nucleases. Class 2 Type II nucleases of the invention can be SpCas9 as described in WO2014093661 or WO2013176772, SaCas9, CjCas9, St1Cas9, NmCas9, FnCas9, RHA FnCas9 in Wang et al (2020), xCas9 (Hu et al, 2018), Cas9-NG (Nishimasu et al, 2018).

Step 3=Identify the location of the cutting/cleavage site and the desired successive deletions/insertions necessary to modify the targeted nucleotide codon The most common NHEJ repair errors observed at a cutting site are deletions of 1 to 3 nucleotides and insertions of 1 nucleotide.

With the Cas9 endonuclease, the two nuclease domains in Cas9 will each cleave one of the DNA strands 3 bases upstream of the PAM, leaving a blunt end DNA double stranded break (DSB). Deletion of the $4^{th}$, of the $4^{th}$ and $5^{th}$, or of the $4^{th}$, $5^{th}$ and 6th nucleotide or insertions of one nucleotide at the $4^{th}$ position upstream (5') of the PAM sequence are frequent modifications introduced in the wild type sequence.

Step 4=Design of the primary guide to cleave the double stranded DNA at the desired position in the wild-type sequence and of the following guides specific of the successive desired deletion or insertion events (it is reminded that a guide RNA and a Cas endonuclease can form a complex that is capable of introducing a double strand break in the target sequence, and that said blunt double strand break (also designated as a cut) is generally repaired with a nucleotide insertion or one to three nucleotide deletions Step 5=Introduction of the guides RNA (or an expression cassette encoding the guides RNA) and the endonuclease (or an expression cassette encoding the endonuclease) in a cell or in a plurality of cells to obtain a modified codon The delivery of the codon-rewrite machinery depends on the targeted cells. The person skilled in the art knows how to adapt the delivery method.

The codon-rewrite machinery can be delivered by way of example as expression cassettes in nucleic acid vectors or as ribonucleoprotein complexes.

Step 6=Screen cells to identify the edited cells having the desired codon modification The total DNA of the cells is extracted, and the targeted region is amplified with adequate primers and sequenced. The targeted region is aligned with the wild type sequence and the introduction of the editing is verified.

The identification of the edited cells can be made by extracting total RNA or total protein.

It is also possible to identify edited cells visually for example if the codon modification introduces a morphological difference or a resistance.

If the edited cells are plant cells, the edited cells can be regenerated into edited plants. The skilled-person knows the regeneration method suitable for each plant.

Before starting the codon re-write method, it is possible to test the targeted region within the targeted nucleic acid sequence of interest with a guide RNA in order to determine the frequencies of deletions and insertions of each potential nucleotide obtained with the cellular DNA repair machinery.

In order to perform this test, the guide RNA is provided with the chosen endonuclease into cells. The cells are maintained in adequate conditions for the editing. The total DNA of the cells is extracted, the targeted region is amplified with adequate primers and the amplicons are sequenced.

The frequencies of deletions and insertions of the four nucleotides at the targeted region can thus be measured.

This step is helpful to optimize the design of the guides towards the most probable insertions or deletions events at the location of the cut.

In some cases, the modification of a codon can be performed through several different scenarios of deletions and insertions. This step can increase the final efficiency by allowing to design of the guides based on the more probable scenario.

FIGURES

FIG. 1 The design of the spacer sequence of the primary guide RNA targeting the Asp94 codon of the wild type sequence. The upper nucleic acid sequence represents the targeted region in ZmHRC (SEQ ID NO:1) In upper case, it represents the codon that needs to be replaced (GAT encoding Asp). The underlined bases are the PAM sequence recognized by Cas9. The lower nucleic acid sequence represents the ZmHRC_Asp94 spacer design (SEQ ID NO: 3) that will be used in the primary guide RNA for the wild type sequence.

FIG. 2 Most common indels in ZmHRC target region The wild-type sequence is shown at the top (SEQ ID NO:43). The target sequence is shown in the rectangle; the PAM sequence is underlined; the deletions are shown by dashed lines; codon of Asp94 is in bold. (SEQ ID NO: 44 to 48)

FIG. 3 Repartition of indel types in ZmHRC among 105 edited T0 plants

FIG. 4 The design of the spacer sequence of the secondary guide RNA targeting the Asp94 codon. The upper nucleic acid sequence represents the targeted region in ZmHRC (SEQ ID NO:1) with the deletion of the three nucleotides (del3) of the GAT codon. The underlined bases are the PAM sequence recognized by Cas9. The lower nucleic acid sequence represents the ZmHRC_Asp94-del3 specific spacer design (SEQ ID NO: 12) that will be used in the guide RNA.

FIG. 5 The design of the spacer sequence of the tertiary guide RNA targeting the Asp94 codon. The upper nucleic acid sequence represents the targeted region in ZmHRC (SEQ ID NO:1) with the deletion of the three nucleotides of the GAT codon and an insertion of one T (del3insT). The underlined bases are the PAM sequence recognized by Cas9.

The lower nucleic acid sequence represents the ZmHRC_Asp94-del3insT specific spacer design (SEQ ID NO: 15) that will be used in the guide RNA.

FIG. 6 The design of the spacer sequence of the quaternary guide RNA targeting the Asp94 codon. The upper nucleic acid sequence represents the targeted region in ZmHRC (SEQ ID NO:1) with the deletion of the three nucleotides of the GAT codon and an insertion of two T (del3insTT). The underlined bases are the PAM sequence recognized by Cas9. The lower nucleic acid sequence represents the ZmHRC_Asp94-del3insTT specific spacer design (SEQ ID NO: 18) that will be used in the guide RNA.

FIG. 7 ZmHRC_Asp-94-Phe complete codon rewrite (SEQ ID NO:49)

FIG. 8 The design of the spacer sequence of the primary guide RNA targeting the Val286 codon of the wild type sequence. The upper nucleic acid sequence represents the targeted region in TaLox1. In upper case, it represents the codon that needs to be replaced (GTC encoding Val). The second nucleic acid sequence is the complementary strand. The underlined bases are the PAM sequence recognized by Cas9. The lower nucleic acid sequence represents the TaLox1_Val286 specific spacer (SEQ ID NO: 21) that will be used in the guide RNA for the wild type sequence.

FIG. 9 Most common indels in TaLox1 Target region on chromosomes B and D. The wild-type sequence is shown on the top (SEQ ID NO: 50). The target sequence is shown in the rectangle; the PAM sequence is underlined; the deletions are shown by dashed lines; codon of Val286 is in bold. (SEQ ID NO: 51 to 55)

FIG. 10 Repartition of indel types in TaLox1 among 51 edited T0 plants

FIG. 11 The design of the spacer sequence of the secondary guide RNA targeting the Val286 codon. The upper nucleic acid sequence represents the targeted region in TaLox1 with the deletion of 2 nucleotides (del2). The second nucleic acid sequence is the complementary strand. The underlined bases are the PAM sequence recognized by Cas9. The lower nucleic acid sequence represents the TaLox1_Val286-del2 specific spacer design (SEQ ID NO: 27) that will be used in the guide RNA.

FIG. 12 The design of the spacer sequence of the tertiary guide RNA targeting the Val286 codon. The upper nucleic acid sequence represents the targeted region in TaLox1 with the deletion of 2 nucleotides and the addition of one A (del2insA). The second nucleic acid sequence is the complementary strand. The underlined bases are the PAM sequence recognized by Cas9. The lower nucleic acid sequence represents the TaLox1_Val286-del2insA specific spacer design (SEQ ID NO: 30) that will be used in the guide RNA.

FIG. 13 TaLox1_Val-286-Glu partial codon rewrite (SEQ ID NO: 56)

FIG. 14 The design of the spacer sequence of the primary guide RNA targeting the Ser621 codon of the wild type sequence. The upper nucleic acid sequence represents the targeted region in ZmALS2. In upper case, it represents the codon that needs to be replaced (AGT encoding Ser). The underlined bases are the PAM sequence recognized by Cas9. The lower nucleic acid sequence represents the Zm_ALS2_Ser621 specific spacer design (SEQ ID NO: 35) that will be used in the guide RNA for the wild type sequence.

FIG. 15 The design of the spacer sequence of the secondary guide RNA targeting the Ser621 codon. The upper nucleic acid sequence represents the targeted region in ZmALS2 with a deletion of the G in the targeted codon (del1). The underlined bases are the PAM sequence recognized by Cas9. The lower nucleic acid sequence represents the ZmALS2_Ser621-del1 specific spacer design (SEQ ID NO: 38) that will be used in the guide RNA.

FIG. 16 ZmALS2 Ser-621-Asn partial codon rewrite (SEQ ID NO: 57)

EXAMPLES

Example 1: Complete Codon Rewrite: Codon Rewrite Machinery Targeting the HRC Gene in Maize A) Identification of the Target Codon.

The chosen target is the *Fusarium* Head Blight susceptibility gene HRC (Su et al.), a gene that encodes a putative histidine-rich calcium-binding protein from *Triticum aestivum* (GenBank: MK450306.1). A maize HRC gene (*Zea* maize cvA188) was identified (SEQ ID NO: 1). The target codon GAT encoding an Aspartic Acid amino acid (Asp) at position 94 in ZmHRC protein (SEQ ID NO: 2) is intended to be replaced by TTT or TTC to encode a Phenylalanine amino acid (Phe) at the same position. The desired replacement is a Asp-94-Phe mutation in ZmHRC.

A primary gRNA targeting Asp94 codon in SEQ ID NO: 1 was designed on the coding strand to introduce a cleavage point after Asp94 codon of the wild type sequence. (FIG. 1)

The expected cleavage site by the Cas9 nuclease is situated three bases upstream (5') of the PAM site (underlined). The cleavage is situated after the T in the GAT codon for Asp94.

B) Genome Editing in Maize Plant Cells by Delivering CRISPR Cas9 and Guide RNA and Regenerating Maize Plants A Cas9 gRNA guide is designed (SEQ ID NO: 4) to target the cleavage site described in Example 1 A) and the nucleic acid expressing said guide is cloned into high copy number plasmids behind a maize U6 promoter (SEQ ID NO: 5) to form SEQ ID NO: 6.

The Cas9 gene from *Streptococcus pyogenes* was codon-optimized for Poaceae using standard techniques known in the art (SEQ ID NO: 7) and nuclear localisation signals (NLS) were added at both ends: Simian virus 40 (SV40) monopartite amino terminal NLS encoded by SEQ ID NO: 8 and *Xenopus laevis* Nucleoplasmin NLS encoded by SEQ ID NO: 9 at the amino- and carboxyl-termini respectively. The optimized sequence of Cas9 was cloned by standard methods under control of the maize ubiquitin promoter and first intron (Christensen et al.) and *Agrobacterium tumefaciens* NOS terminator (Depicker et al.)

The Cas9 expression cassette and the gRNA cassette(s) were introduced into a binary vector pMRT with reporter and selectable marker cassettes to form pBIOS12094 vector and transformed into *Agrobacterium* strain Super virulent LBA4404/pSB1 (Komari et al.)

Maize A188 immature embryos were transformed with pBIOS12094 in *Agrobacterium* strain super virulent LBA4404/pSB1 and plants regenerated according to the procedure described by Ishida et al, 2007.

C) Analysis of the Mutation Profile Obtained with the Primary Guide

To detect the editing, the DNA from the regenerated maize plants is extracted from leave samples and the Asp94 target site is amplified using primers PP_03359_F (SEQ ID NO: 10) and PP_03359_R (SEQ ID NO: 11). Amplicons are sequenced using Next Generation Sequencing (NGS) technology. The number of sequences with indels of at least 1 nucleotide in a 10-nucleotide region centred on the Asp94 target site is assessed. (FIG. 2)

The repartition of the indel types in 105 T0 transgenic plants is shown in FIG. 3.

The deletions of 3 nucleotides and insertions of 1 nucleotide at the locus of Asp94 needed for the Asp-94-Phe mutation are possible and frequent. Additionally, insertions of T nucleotides are frequent among the insertions of 1 nucleotide.

TABLE 1

Repartition of nucleotides among insertions of 1 nucleotide in ZmHRC at Asp94 target locus

| Nucleotide | Frequency of insertion |
|---|---|
| A | 3% |
| T | 97% |
| G | 0% |
| C | 0% |

The replacement of GAT by TTT for the codon of Asp94 can occur at a reasonable frequency. The expected modifications are a deletion of the three nucleotides of the GAT codon and three successive additions of T.

D) Design of the Secondary Guide RNA

Among the various mutations which can be obtained using the primary guide, the deletion of three nucleotides (GAT) is desired (del3). The secondary guide is designed to be specific of the ZmHRC sequence with the deletion of the three nucleotides (GAT) of Asp94 codon. (FIG. 4)

A Cas9 gRNA guide (SEQ ID NO: 13) is designed to target ZmHRC_Asp94-del3, the nucleic acid expressing said guide is cloned into high copy number plasmids behind a maize U6 promoter (SEQ ID NO: 5) to form SEQ ID NO: 14.

E) Design of the Tertiary Guide RNA.

Among the various mutations which can be obtained using the secondary guide, the insertion of 1 nucleotide (T) is desired (del3insT). The tertiary guide is designed to be specific of the ZmHRC_Asp94-del3 sequence with insertion of 1 nucleotide (T) in ZmHRC_Asp94-del3. (FIG. 5)

A Cas9 gRNA guide (SEQ ID NO: 16) is designed to target ZmHRC_Asp94-del3insT and the nucleic acid expressing said guide is cloned into high copy number plasmids behind a maize U6 promoter (SEQ ID NO: 5) to form SEQ ID NO: 17.

F) Design of the Quaternary Guide RNA.

Among the various mutations which can be obtained using the tertiary guide, the insertion of 1 nucleotide (T) is desired (del3insTT). The quaternary guide is designed to be specific of the ZmHRC_Asp94-del3insTT sequence with insertion of 1 nucleotide (T) in ZmHRC_Asp94-del3insT. (FIG. 6)

A Cas9 gRNA guide (SEQ ID NO: 19) is designed to target ZmHRC_Asp94-del3insTT and the nucleic acid expressing said guide is cloned into high copy number plasmids behind a maize U6 promoter (SEQ ID NO: 5) to form SEQ ID NO: 20.

Among the various mutations which can be obtained using the quaternary guide, the insertion of 1 nucleotide (T) will occur, thus generating the desired ZmHRC_Asp-94-Phe codon rewrite. (FIG. 7)

G) Codon Rewrite in Maize Plant Cells by Delivering CRISPR Cas9 and Guide RNA and Regenerating Maize Plants The Cas9 expression cassette and the gRNA cassettes for the primary, secondary, tertiary and quaternary guides were introduced into a binary vector pMRT with reporter and selectable marker cassettes to form pZmHRC_Asp-94-Phe_Cd-RW vector and transformed into Super virulent *Agrobacterium* strain LBA4404/pSB1 (as in example 1A).

Maize A188 immature embryos are transformed with pZmHRC_Asp-94-Phe_Cd-RW in *Agrobacterium* strain super virulent LBA4404/pSB1 and plants are regenerated according to the procedure described in example 1B.

H) Analysis of the Mutation Profile Obtained in Maize Plants

To detect the editing, the DNA from the regenerated maize plants, DNA is extracted from leave samples and the ZmHRC_Asp94 target site is amplified using primers PP_03359_F (SEQ ID NO: 10) and PP_03359_R (SEQ ID NO: 11). Amplicons are sequenced using Next Generation Sequencing (NGS) technology. Plants containing the desired Asp-94-Phe codon rewrite are identified and their phenotype evaluated in presence of the *Fusarium* pathogen.

Example 2: Partial Codon Rewrite: Codon Rewrite Machinery Targeting the Lox1 Gene in Wheat A) Identification of the Target Codon.

The chosen target is the lipoxygenase 1 gene (Lox1) from *Triticum aestivum* (GenBank: GQ166692.1) coding for a 9-lipoxigenase. The silencing of this gene renders wheat resistant to *Fusarium* headblight.

In this experiment to modify the Lox1 gene, the target codon GTC encoding a Valine amino acid (Val) at position 286 in TaLox1 is replaced by GAA or GAG to encode a Glutamic acid amino acid (Glu) at the same position. The desired replacement is a Val-286-Glu mutation in TaLox1.

A functional gRNA targeting TaLox1 has been identified by Wang et al, 2018 on the complementary strand. This guide was chosen to design the primary guide. (FIG. 8)

The expected cleavage site by the Cas9 nuclease is situated three bases upstream (5') of the PAM site after the G in the codon for Val286 of the Lox1 protein as shown by Wang et al, 2018.

According to the codon table, Asp is encoded either by GAA or GAG. The minimum path for the Val-286-Glu mutation involves the replacement of the last 2 nucleotides (TC) of the GTC codon by AA or AG.

B) Genome Editing in Wheat Plant Cells by Delivering CRISPR Cas9 and Guide RNA and Regenerating Wheat Plants A Cas9 gRNA guide (SEQ ID NO: 22) is designed to target the site described in Example 2 A) and the nucleic acid expressing said guide is cloned into high copy number plasmids behind a wheat U6 promoter (SEQ ID NO: 23) to form SEQ ID NO: 24.

The Cas9 expression cassette and the gRNA cassette(s) were introduced into a binary vector pMRT with reporter and selectable marker cassettes to form pBIOS12093 vector and transformed into *Agrobacterium* strain EHA105.

Wheat immature embryos are transformed, selected and regenerated as described by Ishida et al, 2015.

C) Analysis of the Mutation Profile Obtained with the Primary Guide

To detect the editing, the DNA from the wheat plants is extracted from leave samples and the Val286 target site is amplified using primers PP_03344_F (SEQ ID NO: 25) and PP_03344_R (SEQ ID NO: 26). Amplicons are sequenced using Next Generation Sequencing (NGS) technology. The number of sequences with indels of at least 1 nucleotide in a 10-nucleotide region centred on Val286 target site is assessed (FIG. 9).

The repartition of the indel types in 51 T0 transgenic plants is shown in FIG. 10.

The deletions of 2 nucleotides and insertions of 1 nucleotide at the locus of Val286 needed for the Val-286-Glu mutation are therefore possible. Additionally, all 4 nucleotides types are found among the insertions of 1 nucleotide.

TABLE 2

Repartition of nucleotides among insertions of 1 nucleotide in TaLox1 at Val286 target locus

| Nucleotide | Frequency of insertion |
|---|---|
| A | 66% |
| T | 26% |
| G | 4% |
| C | 4% |

The replacement of TC by AA or AG in the GTC codon of Val286 can occur at a reasonable frequency. The replacement AA should occur at a higher frequency than AG.

D) Design of the Secondary Guide RNA.

Among the various mutations which can be obtained using the primary guide, the deletion of two nucleotide (TC) is desired. The secondary guide is designed to be specific of the TaLox1 sequence with the deletion of two nucleotides (TC) of the Val286 codon. (FIG. 11)

A Cas9 gRNA guide (SEQ ID NO: 28) is designed to target TaLox1_Val286-del2 and the nucleic acid expressing said guide is cloned into high copy number plasmids behind a wheat U6 promoter (SEQ ID NO: 23) to form SEQ ID NO: 29.

E) Design of the Tertiary Guide RNA.

Among the various mutations which can be obtained using the secondary guide, the insertion of A or G nucleotide is desired. The frequency of A insertions being higher at the target locus (Example 2C) the insertion of A is preferred. The tertiary guide is designed to be specific of the TaLox1_Val286-del2 sequence with the insertion of 1 nucleotide (A) in TaLox1_Val286-del2. (FIG. 12)

A Cas9 gRNA guide (SEQ ID NO: 31) is designed to target TaLox1_Val286-del2insA and the nucleic acid expressing said guide is cloned into high copy number plasmids behind a wheat U6 promoter (SEQ ID NO: 23) to form SEQ ID NO: 32.

Among the various mutations which can be obtained using the tertiary guide, the insertion of A will occur generating the desired Val-286-Glu codon rewrite. (FIG. 13)

F) Codon Rewrite in Wheat Plant Cells by Delivering CRISPR Cas9 and Guide RNAs and Regenerating Wheat Plants The Cas9 expression cassette and the gRNA cassettes for the primary, secondary and tertiary guides were introduced into a binary vector with reporter and selectable marker cassettes to form pTaLox1_Val-286-Glu_Cd-RW vector and transformed into *Agrobacterium* strain EHA105.

Wheat immature embryos are transformed, selected and regenerated as described by Ishida et al, 2015.

G) Analysis of the Mutation Profile Obtained with the Primary Guide

To detect the editing, the DNA from the wheat plants is extracted from leave samples and the Val286 target site is amplified using primers PP_03344_F (SEQ ID NO: 25) and PP_03344_F (SEQ ID NO: 26). Amplicons are sequenced using Next Generation Sequencing (NGS) technology. Plants containing the desired Val-286-Glu codon rewrite are identified and their phenotype evaluated.

Example 3: Partial Codon Rewrite: Codon Rewrite Machinery Targeting the ZmAHAS Gene for Herbicide Tolerance in Maize A) Identification of the Target Codon.

The chosen target is the herbicide and selectable marker gene acetohydroxyacid synthase (AHAS or ALS). The substitution of a Serine (Ser) by an Asparagine (Asn) at position 621 in the maize ALS protein lead to resistance of maize callus to sulfonylurea herbicides such as chlorosulfuron or imazethapyr (Zhu et al.). Maize has two ALS genes: ALS1 (SEQ ID NO: 33) and ALS2 (SEQ ID NO: 34). Guide RNAs (gRNAs) are designed to introduce the Ser-621-Asn mutation into ZmALS2.

The target codon AGT encoding a Serine amino acid (Ser) at position 621 in ZmALS2 has to be replaced by AAT or AAC to encode an Asparagine amino acid (Asn) at the same position to introduce an herbicide resistance in maize. The desired replacement is a Ser-621-Asn mutation in ZmALS2.

The base replacement to introduce the Ser-621-Asn mutation requires the following minimal change: the deletion of G in AGT and a replacement with A to recreate AAT.

B) Design of a Primary Guide RNA

An optimal Cas9 PAM sequence is identified in the vicinity of the targeted nucleotide ZmALS2 as to introduce a cut directly after the targeted G in the Ser621 codon. (FIG. 14)

A Cas9 gRNA guide is designed (SEQ ID NO: 36) and the nucleic acid expressing said guide is cloned into high copy number plasmids behind a maize U6 promoter (SEQ ID NO: 5) to form SEQ ID NO: 37.

C) Design of a Secondary Guide RNA

Among the various mutations which can be obtained using the primary guide, the deletion of one nucleotide (G) is desired. The secondary guide is designed to be specific of the ZmALS2 sequence with the deletion of one nucleotide (G) in ZmALS2_Ser 621. (FIG. 15)

A Cas9 gRNA guide (SEQ ID NO: 39) is designed to target ZmALS2_Ser621-del1 and the nucleic acid expressing said guide is cloned into high copy number plasmids behind a maize U6 promoter (SEQ ID NO: 5) to form SEQ ID NO: 40.

The secondary guide will introduce a cleavage at the location of the deleted G to induce new mutations at this site. Some of these mutations will be insertions of nucleotide (A) to form Ser-621-Asn mutation into ZmALS2 (FIG. 16).

D) Codon Rewrite in Maize Protoplasts

In one experiment, both the primary gRNA (ID SEQ NO:37) and secondary gRNA (ID SEQ NO:40) plasmids are co-transformed with Cas9 cassette and a reporter cassette into maize A188 protoplasts using a standard PEG-based protocol (Cao et al.)

To detect the editing, the DNA from the maize protoplasts is extracted and the Ser-621-Asn target site is amplified using primers ZmALS_621_for (SEQ ID NO: 41) and ZmALS_621_rev (SEQ ID NO: 42). Amplicons are sequenced using Next Generation Sequencing (NGS) technology. The number of sequences with the desired G to A (Ser-621-Asn) edit is assessed to determine the relative efficiency of codon rewrite.

E) Codon Rewrite in Maize Callus

In a second experiment, the Cas9 expression cassette and both the primary gRNA (ID SEQ NO: 37) and secondary gRNA (ID SEQ NO: 40) were introduced into a binary vector pMRT with reporter and selectable marker cassettes to form pZmALS2_Ser-621-Asn_Cd-RW vector.

pZmALS2_Ser-621-Asn_Cd-RW is introduced into maize Black Mexican Sweet (BMS) cell suspensions by biolistic as described by Kirihara, 1994. Individual chlorosulfuron-resistant calli are isolated and DNA extracted by standard protocol.

The Ser-621-Asn target site is amplified using primers ZmALS_621_for (SEQ ID NO: 41) and ZmALS_621_rev (SEQ ID NO: 42). Amplicons are sequenced to confirm the specific codon rewrite.

F) Codon Rewrite to Obtain Herbicide Tolerance Maize Plants by Targeting the AHAS Gene In a third experiment, pZmALS2_Ser-621-Asn_Cd-RW is transformed into *Agrobacterium* strain Super virulent LBA4404/pSB1 (Komari et al.) and used to transform maize A188 immature embryos and plants regenerated according the procedure described by Ishida et al, 2007.

On T0 plants, the Ser-621-Asn target site is amplified using primers ZmALS_621_for (SEQ ID NO: 41) and ZmALS_621_rev (SEQ ID NO: 42). Amplicons are sequenced to confirm the specific codon rewrite and evaluate the frequency. Chlorosulfuron resistance is confirmed on T1 plants as described by Svitashev et al, 2015.

REFERENCES

Cao, Jianmei & Yao, Dongmei & Lin, Fan & Jiang, Mingyi. (2014). PEG-mediated transient gene expression and silencing system in maize mesophyll protoplasts: A valuable tool for signal transduction study in maize. Acta Physiologiae Plantarum. 36. 1271-1281.

Christensen et al., 1996, *Transgenic. Res.,* 5:213

Cong, L. et al. *Science* 339, 819-823 2013

Depicker et al., Nopaline synthase: transcript mapping and DNA sequence, Journal of Molecular and Applied Genetics, 1982

Hu J H, Miller S M, Geurts M H, Tang W, Chen L, Sun N, Zeina C M, Gao X, Rees H A, Lin Z, Liu D R. Evolved Cas9 variants with broad PAM compatibility and high DNA specificity. *Nature.* 2018 Apr. 5; 556(7699):57-63.

Ishida Y, Hiei Y, Komari T. *Agrobacterium*-mediated transformation of maize. *Nat Protoc.* 2007; 2(7):1614-1621.

Jinek, M. et al. *Science* 337, 816-821 2012

Kim, J. Precision genome engineering through adenine and cytosine base editing. *Nature Plants* 4, 148-151 (2018).

Kirihara, J. A. (1994) in The Maize Handbook, eds. Freeling, M. & Walbot, V. (Springer, New York), pp. 690-694.

Komari T, Hiei Y, Saito Y, Murai N, Kumashiro T. Vectors carrying two separate T-DNAs for co-transformation of higher plants mediated by *Agrobacterium tumefaciens* and segregation of transformants free from selection markers. *Plant J.* 1996; 10:165-174.

Lieber, M. R. The mechanism of double-strand DNA break repair by the nonhomologous DNA end-joining pathway. Annu. Rev. Biochem. 79, 181-211 (2010).

Nishimasu, H., Shi, X., Ishiguro, S., Gao, L., Hirano, S., Okazaki, S., . . . & Oura, S. (2018). Engineered CRISPR-Cas9 nuclease with expanded targeting space. Science, 361(6408), 1259-1262. H. A. Rees, D. R. Liu. Base editing: precision chemistry on the genome and transcriptome of living cells. Nat. Rev. Genet., 19 (2018), pp. 770-788

Rees, H. A., Liu, D. R. Base editing: precision chemistry on the genome and transcriptome of living cells. *Nat Rev Genet* 19, 770-788 (2018)

Ren et al, Molecular Plants, 12 (7), 2019, 1015-1026).

Su, Z., Bernardo, A., Tian, B. et al. A deletion mutation in TaHRC confers Fhb1 resistance to *Fusarium* head blight in wheat. *Nat Genet* 51, 1099-1105 (2019).

Svitashev Sergei, Joshua K. Young, Christine Schwartz, Huirong Gao, S. Carl Falco, A. Mark Cigan. Targeted Mutagenesis, Precise Gene Editing, and Site-Specific Gene Insertion in Maize Using Cas9 and Guide RNA Plant Physiology October 2015, 169 (2) 931-945.

Wang, J, Zhang, C, Feng, B. The rapidly advancing class 2 CRISPR-Cas technologies: A customizable toolbox for molecular manipulations. *J Cell Mol Med.* 2020; 24: 3256-3270.

Wang W, Pan Q, He F, et al. Transgenerational CRISPR-Cas9 Activity Facilitates Multiplex Gene Editing in Allopolyploid Wheat. CRISPR J. 2018; 1(1):65-74.

Zhu T, Peterson D J, Tagliani L, St Clair G, Baszczynski C L and Bowen B (1999). Targeted manipulation of maize genes in vivo using chimeric RNA/DNA oligonucleotides. Proc Natl Acad Sci USA. 96(15):8768-73.

The invention claimed is:

1. A method for introducing a specific mutation at a specified position in a target gene of a cell of an organism, comprising:

(a) introducing together, into a plurality of cells of the organism:

an endonuclease protein;

a first guide RNA that specifically recognizes a targeted position in the target gene;

a second guide RNA that specifically recognizes a modified targeted position generated in step (i); and a third guide RNA that specifically recognizes a second modified targeted position generated in step (ii), (i) wherein the first guide RNA directs the nuclease to cleave the target gene at the targeted position to generate a first cleavage site, wherein a deletion of 2 or 3 nucleotides is introduced by repair at the first cleavage site to form a first modified targeted position;

(ii) wherein the second guide RNA directs the nuclease to cleave the target gene at the first modified targeted position to generate a second cleavage site, wherein a first desired nucleotide being different from the original nucleotide is inserted by repair at this position, to form a second modified targeted position;

(iii) wherein the third guide RNA directs the nuclease to cleave the target gene at the second modified targeted position to generate a third cleavage site, wherein a second desired nucleotide is inserted by repair at the third cleavage site to form a third modified targeted position, and wherein the third modified targeted position is further processed in step (iv) when the deletion in step (i) comprises 3 nucleotides; and (iv) when the deletion in step (i) comprises 3 nucleotides, introducing a fourth guide RNA that specifically recognizes the third modified targeted position, wherein the fourth guide RNA directs the nuclease to cleave the third modified targeted position to generate a fourth cleavage site, wherein a third desired nucleotide is inserted by repair at the fourth cleavage site to form a fourth modified targeted position;

thereby resulting in a cell having a target gene in which two desired nucleotides replace two original nucleotides or three desired nucleotides replace three original nucleotides, without introducing a frameshift; and (b) optionally, screening the plurality of cells to isolate the cell in which the specific mutation has been introduced.

2. The method of claim 1, wherein the endonuclease is selected from SpCas9, SaCas9, CjCas9, St1Cas9, NmCas9, FnCas9, RHA FnCas9, xCas9, and Cas9-NG.

3. The method of claim 1, wherein the deletion in step (i) comprises three nucleotides and the method comprises introducing the fourth guide RNA.

4. The method of claim 3, wherein the endonuclease is selected from SpCas9, SaCas9, CjCas9, St1Cas9, NmCas9, FnCas9, RHA FnCas9, xCas9, and Cas9-NG.

5. The method of claim 1, wherein the specified position is a codon of a gene encoding a protein, and wherein the replacement of the nucleotides results in a change in the amino acid encoded by the codon.

6. The method of claim 5, wherein the endonuclease is selected from SpCas9, SaCas9, CjCas9, St1Cas9, NmCas9, FnCas9, RHA FnCas9, xCas9, and Cas9-NG.

7. The method of claim 1, wherein the specified position spans two codons of a gene encoding a protein, and wherein replacement of the nucleotides results in substitution of two amino acids in the protein.

8. The method of claim 7, wherein the endonuclease is selected from SpCas9, SaCas9, CjCas9, St1Cas9, NmCas9, FnCas9, RHA FnCas9, xCas9, and Cas9-NG.

9. The method of claim 1, wherein the plurality of cells comprises a tissue or a suspension of cells of the organism.

10. The method of claim 9, wherein the endonuclease is selected from SpCas9, SaCas9, CjCas9, St1Cas9, NmCas9, FnCas9, RHA FnCas9, xCas9, and Cas9-NG.

11. The method of claim 1, wherein the mutation is the comprises replacement of two or three nucleotides in the target gene.

12. The method of claim 1, wherein the endonuclease and the guide RNAs are introduced into the plurality of cells by a DNA vector or as ribonucleoproteins (RNPs).

13. The method of claim 1, further comprising recovering cells in which the target gene has been mutated.

14. The method of claim 1, wherein the organism is a plant.

15. The method of claim 14, further comprising regenerating a plant from the plurality of cells, wherein the plant comprises at least one cell containing the mutation at the specified position of the target gene.

16. The method of claim 12, wherein the plurality of cells is cultured to form a callus, and the plant is regenerated from the callus.

17. A method for producing a plant comprising at least one cell containing a mutation at a specified position of a target gene, comprising:

performing the method of claim 1 on a plurality of plant cells; and regenerating the plant from the plurality of cells.

* * * * *

SEQUENCE LISTING

```
<160> NUMBER OF SEQ ID NOS: 86

<210> SEQ ID NO 1
<211> LENGTH: 2754
<212> TYPE: DNA
<213> ORGANISM: Zea mays

<400> SEQUENCE: 1

aggggggtgtt tgggagtgaa gttttttcac agttttggaa gaatactgca gtattctcaa      60

atactgcagt attatataca gaatggtgtt tggcaagcta gctaaaatct ctgttttcaa     120

aactgaagta ttgcaaatac tatagttgtt ttaaggcatt ctaaacttag ctctggacct     180

cagttttcaa aactgcggta ttgtaaactg cggtattgtc atgactaaag tatactgtag     240

tatttcaaaa actgtggttt tcaaaaactt tattcccaaa cagggcctga cctgtatgtt     300

tgtttacgtc ggcctagatg tatgtgcacc tgctgtctta taaaattgtc ggccttggcc     360
```

-continued

```
caagccaagg accctttcgc ttctctcagt ctacgactag gcggcggcgg cggccttcac    420
gcacgagcct tcgccgccta tacttgcgct tcgtcgagcc ggtgagtccc attcttgccc    480
tcttattttg cgttttctcc aaatcttttc ctgacaaaaa tcgacgatgt ttgttttgag    540
tttcctccag catgaagaaa tcgttgaatt tttaaagtat atgatgctat gatgctagcg    600
cgtttgggtt ccagatcggg gtgagtggag ccagatctgt gagctgcagg ggttaaatgt    660
cgtaaagcgc agttagggtt tgggggtgac ggtggcggtg gttctcggct atttttcaga    720
tctgtgatat tttcgagaat tctcgggtgt gttggcttcg agttttgtga gctctctgtt    780
gtgcgatgtg caagtactag gaattggatg tggctgggat ttgagtatgc tctattgcct    840
ctatgcacgg atgacggatg tgtttctctt agtggacaat gaccctttta aattgctttt    900
ctcgaattca tattttccaa ctgtgttttc tttttgttgc tattgcaggt gaattgtggt    960
ctaagcacac gaaggaagga tctttctcca gacttcgcaa ttttggacga cgaggtaagg   1020
aagtgtataa tcgtgcatac tctgtgtttg tttcttggtg gcgactgcaa ttagctttag   1080
tttctcttag tgttagggtc tgtttggata ccaaggctaa ttgctagcta gctaaaattt   1140
agctctagta catccaacat gagagctaat agttgagata ttttttagcc aagtcttcaa   1200
ctagttttta gctaactacc tagccaacca taactaattg agctaattta gccctaacta   1260
gtatctcaaa caggccttta accttcatgc ttgtgcggtg tggttttata aacatgtaac   1320
cacagcttgg ttccaatatt gtattactgt catttcgaaa tataagatgt tggtagttaa   1380
attgattgga actatgtgtc tcttttgctg cacccagatt cataaccata atcatgttta   1440
aacaagtgtt gtatgaagag tcatctttct tttatcaagg gcaactgatt ttggtctacc   1500
atatcgtcct cgcataagta atttttagga tattgcttat aattgtgata cctttgagat   1560
ccctttttgtt aacatagttt tatgagctta aaatcttaga agccatctag ctttgaacat   1620
gattgattgg ccactcttct tagaaagttg tcttgaacaa aaaatgaact gcgtgggtat   1680
tatatgagaa tactttggtt acatttgagg cttaaactag ctcaaagcgc ctccaagtaa   1740
tttgatgcca gggattaatt caccacattt gttatgcctg tacatggaag tttattgtag   1800
aaggctttca atctatctga ttagatttac atctctacta ttgtgctata taatttcaca   1860
agttcaaaaa actaacagtg tttttatctc tcttctatga gatgcacttc cttgcatcat   1920
ttcatgtccc tacaggtttt gtgttatctg gtttgtcggg atggatgcca aaaagttcct   1980
gcagctggtc gaagagaaga aaaggaggat cctcgagaag aaagaagccc cactaaagtg   2040
gcagcagaag ctagaagcag cagttaacgt caaagctgat gcagaagcga aggcgaaaaa   2100
actaaaatca agaaagcata ggaggagagg agattcttcc tcggactctg acagtgacta   2160
tgacagcgat gttgatcgga aacaccggag gaggaaggat cgtagaagga acaagaagca   2220
tgagcattct gactctgatg atgccaggag aggcaagcgt aggtccaaaa agggctcaga   2280
ctcaagtgat gagagcaacc gtgaatatga aagcgggtct gaagaagaac atacaaagaa   2340
gaagcgtttg cacagaagaa ggcatcacag acactcttca aggtcagact ctgaagacaa   2400
cagtgatgag gaagagcgga gatctgccaa ggaccattct cagccccgca gacgccacca   2460
tcagtcttct gatgatggcc cggacaaggt caggttgaga catgggaagc gtctgagatc   2520
aagtgacgag aatgctcggc cagattccaa cagccataag catctcagga gccaatcctt   2580
ggaggagtca tcagatgata gagatgatga tggaccagag aagataagaa atggcaaaag   2640
gtatcacaag aatcatcacc gtcaccacca tcatcatcgt caccatcggc accaccatga   2700
aagacataat aactcagcag aacctaatga caggaggcaa gtactgaaag atga         2754
```

<210> SEQ ID NO 2
<211> LENGTH: 247
<212> TYPE: PRT
<213> ORGANISM: Zea mays

<400> SEQUENCE: 2

```
Met Asp Ala Lys Arg Phe Leu His Leu Val Glu Glu Lys Lys Arg Arg
1               5                   10                  15

Val Leu Glu Lys Lys Glu Ala Pro Leu Lys Trp Glu Gln Lys Leu Glu
            20                  25                  30

Thr Ala Ala Lys Ala Lys Val Asp Ala Glu Ala Lys Val Lys Lys Leu
        35                  40                  45

Asn Ser Arg Lys His Arg Arg Arg Gly Asp Leu Ser Ser Asp Ser Asp
    50                  55                  60

Ser Asp Tyr Gly Ser Asp Val Asp Arg Lys His Leu Lys Arg Lys Asn
65                  70                  75                  80

Arg Arg Arg Asn Lys Lys His Glu His Ser Asp Ser Asp Asp Ala Arg
                85                  90                  95

Arg Arg Asn Arg Arg Ser Arg Arg Ser Thr Asp Ser Ser Asp Glu Ser
            100                 105                 110

Asp Ser Glu Tyr Glu Thr Arg Ser Glu Glu Glu Arg Pro Arg Lys Lys
        115                 120                 125

Arg Ser His Arg Arg Arg His His Arg His Ser Ser Lys Ser Asp Ser
    130                 135                 140

Glu Asn Tyr Ser Ser Asp Glu Glu Gln Arg Arg Pro Ala Lys Asp His
145                 150                 155                 160

Ser Gln Ser Arg Arg Arg His His Arg Ser Ser Asp Asp Asp Ser Asp
                165                 170                 175

Lys Asp Lys Val Lys Ser Arg His Gly Lys Gly Leu Arg Ser Arg Asp
            180                 185                 190

Glu Asp Ala Arg Ala Asp Phe Asn Ser Asn Lys His Leu Arg Ser Gln
        195                 200                 205

Ser Leu Glu Glu Ser Ser Asp Asp Arg Asp Ala Asp Glu Ser Glu Lys
    210                 215                 220

Met Arg Asn Gly Lys Arg Ser His Lys Asn Gly Gly His Arg His His
225                 230                 235                 240

His His Arg His His His Glu
                245
```

<210> SEQ ID NO 3
<211> LENGTH: 20
<212> TYPE: DNA
<213> ORGANISM: Artificial Sequence
<220> FEATURE:
<223> OTHER INFORMATION: ZmHRC_Asp94_for_spacer

<400> SEQUENCE: 3

```
attctgactc tgatgatgcc                                                  20
```

<210> SEQ ID NO 4
<211> LENGTH: 100
<212> TYPE: DNA
<213> ORGANISM: Artificial Sequence
<220> FEATURE:
<223> OTHER INFORMATION: gRNA_ZmHRC_Asp94_for

<400> SEQUENCE: 4

```
attctgactc tgatgatgcc gttttagagc tagaaatagc aagttaaaat aaggctagtc     60

cgttatcaac ttgaaaaagt ggcaccgagt cggtgctttt                          100


<210> SEQ ID NO 5
<211> LENGTH: 398
<212> TYPE: DNA
<213> ORGANISM: Artificial Sequence
<220> FEATURE:
<223> OTHER INFORMATION: ZmU6 promoter

<400> SEQUENCE: 5

aagtcgtaaa atagtggtgt ccaaagaatt tccaggccca gttgtaaaag ctaaaatgct     60

attcaatttc tactagcagt aagtcgtgtt tagaaattat ttttttatat accttttttc    120

cttctatgta cagtaggaca cagtgtcagc gccgcgttga cggagaatat ttgcaaaaaa    180

gtaaaagaga aagtcatagc ggcgtatgtg ccaaaaactt cgtcacagag aggccataag    240

aaacatggcc cacggcccaa tacgaagcac cgcgacgaag cccaaacagc agtccgtagg    300

tggagcaaag cgctgggtaa tacgcaaacg ttttgtccca ccttgactaa tcacaagagt    360

ggagcgtacc ttataaaccg agccgcaagc accgaatt                            398


<210> SEQ ID NO 6
<211> LENGTH: 506
<212> TYPE: DNA
<213> ORGANISM: Artificial Sequence
<220> FEATURE:
<223> OTHER INFORMATION: ZmU6_gRNA_ZmHRC_Asp94_for

<400> SEQUENCE: 6

aagtcgtaaa atagtggtgt ccaaagaatt tccaggccca gttgtaaaag ctaaaatgct     60

attcaatttc tactagcagt aagtcgtgtt tagaaattat ttttttatat accttttttc    120

cttctatgta cagtaggaca cagtgtcagc gccgcgttga cggagaatat ttgcaaaaaa    180

gtaaaagaga aagtcatagc ggcgtatgtg ccaaaaactt cgtcacagag aggccataag    240

aaacatggcc cacggcccaa tacgaagcac cgcgacgaag cccaaacagc agtccgtagg    300

tggagcaaag cgctgggtaa tacgcaaacg ttttgtccca ccttgactaa tcacaagagt    360

ggagcgtacc ttataaaccg agccgcaagc accgaattga ttctgactct gatgatgccg    420

ttttagagct agaaatagca agttaaaata aggctagtcc gttatcaact tgaaaaagtg    480

gcaccgagtc ggtgcttttt tttttt                                         506


<210> SEQ ID NO 7
<211> LENGTH: 4104
<212> TYPE: DNA
<213> ORGANISM: Artificial Sequence
<220> FEATURE:
<223> OTHER INFORMATION: SpCas9 codon optimised

<400> SEQUENCE: 7

atggacaaga agtacagcat cgggctcgac atcgggacga acagcgttgg gtgggcggtc     60

atcacggacg agtacaaggt tccctccaag aagttcaagg tgctggggaa caccgaccgc    120

cactccatca agaagaacct catcggggcc ctcctgttcg acagcgggga gaccgctgag    180

gctacgaggc tcaagagaac cgcgaggcgc agatacacga gaaggaagaa caggatctgc    240

tacctccaag agatcttctc caacgagatg gccaaggttg acgattcatt cttccaccgc    300

ctggaggagt ctttcctcgt ggaggaggac aagaagcacg agcggcatcc catcttcggg    360

aacatcgtcg acgaggttgc ctaccacgag aagtacccta cgatctacca tctgcggaag    420
```

-continued

```
aagctcgtgg acagcaccga taaggcggac ctcagactga tctacctcgc cctggcgcac    480
atgatcaagt tccgcgggca tttcctgatc gaggggggatc tcaacccaga caactccgat    540
gttgacaagc tgttcatcca actcgtgcag acctacaacc aactcttcga ggagaacccg    600
atcaacgctt cgggggtcga cgctaaggcc atcctgtcag cccgcctctc gaagtcacgc    660
aggctggaga acctgatcgc gcagctccca ggggagaaga agaacgggct gttcgggaac    720
ctcatcgctc tctctctggg gctcacgccg aacttcaagt ccaacttcga tctcgccgag    780
gacgcgaagc tgcaactcag caaggacacc tacgacgatg acctcgataa cctcctggcg    840
cagatcgggg atcaatacgc tgacctgttc ctcgccgcga agaacctgtc ggacgccatc    900
ctcctgtcag atatcctccg cgtgaacacc gagatcacga aggccccact ctctgcgtcc    960
atgatcaagc gctacgacga gcaccatcag gatctgaccc tcctgaaggc gctggtccgc   1020
caacagctcc cggagaagta caaggagatc ttcttcgatc agtcgaagaa cgggtacgct   1080
gggtacatcg acgggggggc gtcacaagag gagttctaca agttcatcaa gccaatcctg   1140
gagaagatgg acgggacgga ggagctcctg gtgaagctca acagggagga cctcctgcgg   1200
aagcagagaa ccttcgataa cgggtccatc ccccaccaaa tccatctcgg ggagctgcac   1260
gccatcctga gaaggcaaga ggacttctac cctttcctca aggataaccg ggagaagatc   1320
gagaagatcc tgaccttcag aatcccatac tacgtcgggc cgctcgctcg ggggaacagc   1380
agattcgcct ggatgacccg caagtcggag gagaccatca cgccgtggaa cttcgaggag   1440
gtggtcgaca agggggcgag cgctcagtcg ttcatcgaga ggatgaccaa cttcgacaag   1500
aacctgccca acgagaaggt gctccctaag cactcgctcc tgtacgagta cttcaccgtc   1560
tacaacgagc tcacgaaggt gaagtatgtg accgagggga tgagaaagcc tgccttcctg   1620
tccggggagc agaagaaggc gatcgtggac ctcctgttca agaccaaccg gaaggtcacg   1680
gttaagcaac tcaaggagga ctacttcaag aagatcgagt gcttcgattc ggtggagatc   1740
tcaggggtcg aggacaggtt caacgcctcc ctcgggacct accacgatct cctgaagatc   1800
atcaaggata aggacttcct ggacaacgag gagaacgagg acatcctgga ggacatcgtg   1860
ctgaccctca cgctgttcga ggacagggag atgatcgagg agcgcctgaa gacgtacgcc   1920
catctcttcg atgacaaggt catgaagcaa ctcaagagaa gaagatacac cgggtggggg   1980
aggctgtccc gcaagctcat caacgggatc cgggacaagc agtcagggaa gaccatcctc   2040
gacttcctga agtctgatgg gttcgccaac aggaacttca tgcaactgat ccacgatgac   2100
tcactcacct tcaaggagga tatccaaaag gctcaggtga gcgggcaggg ggactcgctg   2160
cacgagcata tcgctaacct cgctgggtcc cctgcgatca agaaggggat cctgcagacc   2220
gtgaaggttg tggacgagct cgtgaaggtc atggggcggc ataagcctga gaacatcgtc   2280
atcgagatgg ccagagagaa ccaaaccacg cagaaggggc aaaagaactc tagggagcgc   2340
atgaagcgca tcgaggaggg gatcaaggag ctggggtccc aaatcctcaa ggagcaccca   2400
gttgagaaca cccaactgca gaacgagaag ctctacctgt actacctcca gaacgggagg   2460
gatatgtatg tggaccaaga gctggatatc aaccgcctca gcgattacga cgttgatcat   2520
atcgtgcccc agtctttcct gaaggatgac tccatcgaca acaaggtcct caccaggtcg   2580
gacaagaacc gcgggaagtc agataacgtt ccatctgagg aggtcgttaa gaagatgaag   2640
aactactgga ggcagctcct gaacgccaag ctgatcacgc aaaggaagtt cgacaacctc   2700
accaaggctg agagaggggg gctctcagag ctggacaagg ctgggttcat caagcggcag   2760
```

```
ctggtcgaga ccagacaaat cacgaagcac gttgcgcaaa tcctcgactc tcggatgaac   2820

acgaagtacg atgagaacga caagctgatc agggaggtga aggtcatcac cctgaagtct   2880

aagctcgtct ccgacttccg caaggacttc cagttctaca aggttcgcga gatcaacaac   2940

taccaccatg cgcatgacgc ttacctcaac gctgtggtcg ggaccgccct gatcaagaag   3000

tacccgaagc tggagagcga gttcgtgtac ggggactaca aggtttacga tgtgcgcaag   3060

atgatcgcca agtcggagca agagatcggg aaggccaccg ccaagtactt cttctactca   3120

aacatcatga acttctttaa gaccgagatc acgctggcca acggggagat ccggaagaga   3180

cccctcatcg agaccaacgg ggagacgggg gagatcgtgt gggacaaggg gagggatttc   3240

gcgaccgtcc gcaaggttct ctccatgccc caggtgaaca tcgtcaagaa gaccgaggtc   3300

caaacggggg ggttctcaaa ggagtctatc ctgcctaagc ggaacagcga caagctcatc   3360

gccagaaaga aggactggga tccaaagaag tacgggggt tcgacagccc taccgtcgcg   3420

tactcggttc tggttgtggc taaggttgag aaggggaagt ccaagaagct caagagcgtg   3480

aaggagctcc tggggatcac catcatggag cgctccagct tcgagaagaa cccaatcgac   3540

ttcctggagg ccaaggggta caaggaggtg aagaaggacc tgatcatcaa gctcccgaag   3600

tactctctct tcgagctgga gaacgggagg aagcgcatgc tggcttccgc tggggagctc   3660

caaaagggga acgagctcgc cctgccatcc aagtatgtga acttcctcta cctggcgtcc   3720

cactacgaga agctcaaggg gagcccggag gacaacgagc aaaagcagct gttcgtcgag   3780

cagcacaagc attacctcga cgagatcatc gagcaaatct ccgagttctc caagcgcgtg   3840

atcctcgcgg acgctaacct ggataaggtc ctctccgctt acaacaagca ccgggacaag   3900

cccatcagag agcaggccga gaacatcatc catctcttca ccctgacgaa cctcggggcc   3960

cctgctgcct tcaagtactt cgacaccacg atcgatcgga agagatacac cagcacgaag   4020

gaggtcctgg acgcgaccct catccaccaa tctatcacgg ggctgtacga gacgagaatc   4080

gacctgtcac aactgggggg ggac                                          4104
```

<210> SEQ ID NO 8
<211> LENGTH: 42
<212> TYPE: DNA
<213> ORGANISM: Artificial Sequence
<220> FEATURE:
<223> OTHER INFORMATION: SV40 NLS

<400> SEQUENCE: 8

```
atggctccta agaagaagcg caaggttggg atccacgggg tt                        42
```

<210> SEQ ID NO 9
<211> LENGTH: 48
<212> TYPE: DNA
<213> ORGANISM: Artificial Sequence
<220> FEATURE:
<223> OTHER INFORMATION: XlNucleoplasmin NLS

<400> SEQUENCE: 9

```
aagaggccgg cggcaaccaa gaaggcgggc caggccaaga agaagaag                  48
```

<210> SEQ ID NO 10
<211> LENGTH: 20
<212> TYPE: DNA
<213> ORGANISM: Artificial Sequence
<220> FEATURE:
<223> OTHER INFORMATION: PP_03359_F

<400> SEQUENCE: 10
aaaggttcct gcatctggtc 20

<210> SEQ ID NO 11
<211> LENGTH: 22
<212> TYPE: DNA
<213> ORGANISM: Artificial Sequence
<220> FEATURE:
<223> OTHER INFORMATION: PP_03359_R

<400> SEQUENCE: 11
gagtctgact ttgaagagtg cc 22

<210> SEQ ID NO 12
<211> LENGTH: 20
<212> TYPE: DNA
<213> ORGANISM: Artificial Sequence
<220> FEATURE:
<223> OTHER INFORMATION: ZmHRC_Asp94-del3_for_spacer

<400> SEQUENCE: 12
agcattctga ctctgatgcc 20

<210> SEQ ID NO 13
<211> LENGTH: 100
<212> TYPE: DNA
<213> ORGANISM: Artificial Sequence
<220> FEATURE:
<223> OTHER INFORMATION: gRNA_ZmHRC_Asp94-del3_for

<400> SEQUENCE: 13
agcattctga ctctgatgcc gttttagagc tagaaatagc aagttaaaat aaggctagtc 60
cgttatcaac ttgaaaaagt ggcaccgagt cggtgctttt 100

<210> SEQ ID NO 14
<211> LENGTH: 506
<212> TYPE: DNA
<213> ORGANISM: Artificial Sequence
<220> FEATURE:
<223> OTHER INFORMATION: ZmU6_gRNA_ZmHRC_Asp94-del3_for

<400> SEQUENCE: 14
aagtcgtaaa atagtggtgt ccaaagaatt tccaggccca gttgtaaaag ctaaaatgct 60
attcaatttc tactagcagt aagtcgtgtt tagaaattat ttttttatat accttttttc 120
cttctatgta cagtaggaca cagtgtcagc gccgcgttga cggagaatat ttgcaaaaaa 180
gtaaaagaga aagtcatagc ggcgtatgtg ccaaaaactt cgtcacagag aggccataag 240
aaacatggcc cacggcccaa tacgaagcac cgcgacgaag cccaaacagc agtccgtagg 300
tggagcaaag cgctgggtaa tacgcaaacg ttttgtccca ccttgactaa tcacaagagt 360
ggagcgtacc ttataaaccg agccgcaagc accgaattga gcattctgac tctgatgccg 420
ttttagagct agaaatagca agttaaaata aggctagtcc gttatcaact tgaaaaagtg 480
gcaccgagtc ggtgcttttt tttttt 506

<210> SEQ ID NO 15
<211> LENGTH: 20
<212> TYPE: DNA
<213> ORGANISM: Artificial Sequence
<220> FEATURE:
<223> OTHER INFORMATION: ZmHRC_Asp94-del3insT_for_spacer

<400> SEQUENCE: 15
gcattctgac tctgattgcc 20

<210> SEQ ID NO 16
<211> LENGTH: 100
<212> TYPE: DNA
<213> ORGANISM: Artificial Sequence
<220> FEATURE:
<223> OTHER INFORMATION: gRNA_ZmHRC_Asp94-del3insT_for

<400> SEQUENCE: 16
gcattctgac tctgattgcc gttttagagc tagaaatagc aagttaaaat aaggctagtc 60
cgttatcaac ttgaaaaagt ggcaccgagt cggtgctttt 100

<210> SEQ ID NO 17
<211> LENGTH: 505
<212> TYPE: DNA
<213> ORGANISM: Artificial Sequence
<220> FEATURE:
<223> OTHER INFORMATION: ZmU6_gRNA_ZmHRC_Asp94-del3insT_for

<400> SEQUENCE: 17
aagtcgtaaa atagtggtgt ccaaagaatt tccaggccca gttgtaaaag ctaaaatgct 60
attcaatttc tactagcagt aagtcgtgtt tagaaattat tttttatat acctttttc 120 cttctatgta cagtaggaca cagtgtcagc gccgcgttga cggagaatat ttgcaaaaaa 180
gtaaaagaga aagtcatagc ggcgtatgtg ccaaaaactt cgtcacagag aggccataag 240
aaacatggcc cacggcccaa tacgaagcac cgcgacgaag cccaaacagc agtccgtagg 300
tggagcaaag cgctgggtaa tacgcaaacg ttttgtccca ccttgactaa tcacaagagt 360
ggagcgtacc ttataaaccg agccgcaagc accgaattgc attctgactc tgattgccgt 420
tttagagcta gaaatagcaa gttaaaataa ggctagtccg ttatcaactt gaaaaagtgg 480
caccgagtcg gtgctttttt ttttt 505

<210> SEQ ID NO 18
<211> LENGTH: 20
<212> TYPE: DNA
<213> ORGANISM: Artificial Sequence
<220> FEATURE:
<223> OTHER INFORMATION: ZmHRC_Asp94-del3insTT_for_spacer

<400> SEQUENCE: 18
cattctgact ctgatttgcc 20

<210> SEQ ID NO 19
<211> LENGTH: 100
<212> TYPE: DNA
<213> ORGANISM: Artificial Sequence
<220> FEATURE:
<223> OTHER INFORMATION: gRNA_ZmHRC_Asp94-del3insTT_for

<400> SEQUENCE: 19
cattctgact ctgatttgcc gttttagagc tagaaatagc aagttaaaat aaggctagtc 60
cgttatcaac ttgaaaaagt ggcaccgagt cggtgctttt 100

<210> SEQ ID NO 20
<211> LENGTH: 506
<212> TYPE: DNA
<213> ORGANISM: Artificial Sequence
<220> FEATURE:
<223> OTHER INFORMATION: ZmU6_gRNA_ZmHRC_Asp94-del3insTT_for

<400> SEQUENCE: 20
aagtcgtaaa atagtggtgt ccaaagaatt tccaggccca gttgtaaaag ctaaaatgct 60
attcaatttc tactagcagt aagtcgtgtt tagaaattat tttttatat accttttttc 120 cttctatgta cagtaggaca cagtgtcagc gccgcgttga cggagaatat ttgcaaaaaa 180
gtaaaagaga aagtcatagc ggcgtatgtg ccaaaaactt cgtcacagag aggccataag 240
aaacatggcc cacggcccaa tacgaagcac cgcgacgaag cccaaacagc agtccgtagg 300
tggagcaaag cgctgggtaa tacgcaaacg ttttgtccca ccttgactaa tcacaagagt 360
ggagcgtacc ttataaaccg agccgcaagc accgaattgc attctgactc tgatttgccg 420
ttttagagct agaaatagca agttaaaata aggctagtcc gttatcaact tgaaaaagtg 480
gcaccgagtc ggtgcttttt tttttt 506

<210> SEQ ID NO 21
<211> LENGTH: 17
<212> TYPE: DNA
<213> ORGANISM: Artificial Sequence
<220> FEATURE:
<223> OTHER INFORMATION: TaLox1_Val286_rev_spacer

<400> SEQUENCE: 21
gccgggggtg tcgacgt 17

<210> SEQ ID NO 22
<211> LENGTH: 97
<212> TYPE: DNA
<213> ORGANISM: Artificial Sequence
<220> FEATURE:
<223> OTHER INFORMATION: gRNA_TaLox1_Val286_rev

<400> SEQUENCE: 22
gccgggggtg tcgacgtgtt ttagagctag aaatagcaag ttaaaataag gctagtccgt 60
tatcaacttg aaaaagtggc accgagtcgg tgctttt 97

<210> SEQ ID NO 23
<211> LENGTH: 363
<212> TYPE: DNA
<213> ORGANISM: Artificial Sequence
<220> FEATURE:
<223> OTHER INFORMATION: TaU6 promoter

<400> SEQUENCE: 23
gaccaagccc gttattctga cagttctggt gctcaacaca tttatattta tcaaggagca 60
cattgttact cactgctagg agggaatcga actaggaata ttgatcagag gaactacgag 120
agagctgaag ataactgccc tctagctctc actgatctgg gtcgcatagt gagatgcagc 180
ccacgtgagt tcagcaacgg tctagcgctg ggcttttagg cccgcatgat cgggcttttg 240
tcgggtggtc gacgtgttca cgattgggga gagcaacgca gcagttcctc ttagtttagt 300
cccacctcgc ctgtccagca gagttctgac cggtttataa actcgcttgc tgcatcagac 360
ttg 363

<210> SEQ ID NO 24
<211> LENGTH: 466
<212> TYPE: DNA
<213> ORGANISM: Artificial Sequence
<220> FEATURE:
<223> OTHER INFORMATION: TaU6_gRNA_TaLox1_Val286_rev

<400> SEQUENCE: 24
gaccaagccc gttattctga cagttctggt gctcaacaca tttatattta tcaaggagca 60
cattgttact cactgctagg agggaatcga actaggaata ttgatcagag gaactacgag 120
agagctgaag ataactgccc tctagctctc actgatctgg gtcgcatagt gagatgcagc 180
ccacgtgagt tcagcaacgg tctagcgctg ggcttttagg cccgcatgat cgggcttttg 240
tcgggtggtc gacgtgttca cgattgggga gagcaacgca gcagttcctc ttagtttagt 300
cccacctcgc ctgtccagca gagttctgac cggtttataa actcgcttgc tgcatcagac 360
ttgccggggg tgtcgacgtg ttttagagct agaaatagca agttaaaata aggctagtcc 420
gttatcaact tgaaaaagtg gcaccgagtc ggtgcttttt tttttt 466

<210> SEQ ID NO 25
<211> LENGTH: 19
<212> TYPE: DNA
<213> ORGANISM: Artificial Sequence
<220> FEATURE:
<223> OTHER INFORMATION: PP_03344_F

<400> SEQUENCE: 25
agttcggcca cctcaagac 19

<210> SEQ ID NO 26
<211> LENGTH: 20
<212> TYPE: DNA
<213> ORGANISM: Artificial Sequence
<220> FEATURE:
<223> OTHER INFORMATION: PP_03344_R

<400> SEQUENCE: 26
aggtccttga tgagctggag 20

<210> SEQ ID NO 27
<211> LENGTH: 17
<212> TYPE: DNA
<213> ORGANISM: Artificial Sequence
<220> FEATURE:
<223> OTHER INFORMATION: TaLox1_Val286-del2_rev_spacer

<400> SEQUENCE: 27
ctgccggggg tgtccgt 17

<210> SEQ ID NO 28
<211> LENGTH: 97
<212> TYPE: DNA
<213> ORGANISM: Artificial Sequence
<220> FEATURE:
<223> OTHER INFORMATION: gRNA_TaLox1_Val286-del2_rev

<400> SEQUENCE: 28
ctgccggggg tgtccgtgtt ttagagctag aaatagcaag ttaaaataag gctagtccgt 60
tatcaacttg aaaaagtggc accgagtcgg tgcttttt 97

<210> SEQ ID NO 29
<211> LENGTH: 467
<212> TYPE: DNA
<213> ORGANISM: Artificial Sequence
<220> FEATURE:
<223> OTHER INFORMATION: TaU6_gRNA_TaLox1_Val286-del2_rev

<400> SEQUENCE: 29
gaccaagccc gttattctga cagttctggt gctcaacaca tttatattta tcaaggagca 60
cattgttact cactgctagg agggaatcga actaggaata ttgatcagag gaactacgag 120
agagctgaag ataactgccc tctagctctc actgatctgg gtcgcatagt gagatgcagc 180
ccacgtgagt tcagcaacgg tctagcgctg ggcttttagg cccgcatgat cgggcttttg 240
tcgggtggtc gacgtgttca cgattgggga gagcaacgca gcagttcctc ttagtttagt 300
cccacctcgc ctgtccagca gagttctgac cggtttataa actcgcttgc tgcatcagac 360
ttgctgccgg gggtgtccgt gttttagagc tagaaatagc aagttaaaat aaggctagtc 420
cgttatcaac ttgaaaaagt ggcaccgagt cggtgctttt ttttttt 467

<210> SEQ ID NO 30
<211> LENGTH: 17
<212> TYPE: DNA
<213> ORGANISM: Artificial Sequence
<220> FEATURE:
<223> OTHER INFORMATION: TaLox1_Val286-del2insA_rev_spacer

<400> SEQUENCE: 30
tgccgggggt gtcacgt 17

<210> SEQ ID NO 31
<211> LENGTH: 97
<212> TYPE: DNA
<213> ORGANISM: Artificial Sequence
<220> FEATURE:
<223> OTHER INFORMATION: gRNA_TaLox1_Val286-del2insA_rev

<400> SEQUENCE: 31
tgccgggggt gtcacgtgtt ttagagctag aaatagcaag ttaaaataag gctagtccgt 60
tatcaacttg aaaaagtggc accgagtcgg tgcttttt 97

<210> SEQ ID NO 32
<211> LENGTH: 467
<212> TYPE: DNA
<213> ORGANISM: Artificial Sequence
<220> FEATURE:
<223> OTHER INFORMATION: TaU6_gRNA_TaLox1_Val286-del2insA_rev

<400> SEQUENCE: 32
gaccaagccc gttattctga cagttctggt gctcaacaca tttatattta tcaaggagca 60
cattgttact cactgctagg agggaatcga actaggaata ttgatcagag gaactacgag 120
agagctgaag ataactgccc tctagctctc actgatctgg gtcgcatagt gagatgcagc 180
ccacgtgagt tcagcaacgg tctagcgctg ggcttttagg cccgcatgat cgggcttttg 240
tcgggtggtc gacgtgttca cgattgggga gagcaacgca gcagttcctc ttagtttagt 300
cccacctcgc ctgtccagca gagttctgac cggtttataa actcgcttgc tgcatcagac 360
ttgtgccggg ggtgtcacgt gttttagagc tagaaatagc aagttaaaat aaggctagtc 420
cgttatcaac ttgaaaaagt ggcaccgagt cggtgctttt ttttttt 467

<210> SEQ ID NO 33
<211> LENGTH: 1917
<212> TYPE: DNA
<213> ORGANISM: Artificial Sequence
<220> FEATURE:
<223> OTHER INFORMATION: ZmALS1 coding sequence

<400> SEQUENCE: 33
atggccaccg ccgccaccgc ggccgccgcg ctcaccggcg ccactaccgc tacgcccaag 60
tcgaggcgcc gagcccacca cttggccacc cggcgcgccc tcgccgcgcc catcaggtgc 120

```
tcagcgttgt cacgcgccac gccgacggct cccccggcca ctccgctacg tccgtggggc    180
cccaacgagc cccgcaaggg ctccgacatc ctcgtcgagg ctctcgagcg ctgtggcgtc    240
cgtgacgtct tcgcctaccc cggcggcgca tccatggaga tccaccaggc actcacccgc    300
tccccgtca tcgccaacca cctcttccgc cacgaacaag ggaggcctt cgccgcctcc    360
ggctacgcgc gctcctcggg ccgcgttggc gtctgcatcg ccacctccgg ccccggcgcc    420
accaacctag tctctgcgct cgcagacgcg ttgctcgact ccgtccccat tgtcgccatc    480
acgggacagg tgccgcgacg catgattggc accgacgcct ttcaggagac gcccatcgtc    540
gaggtcaccc gctccatcac caagcacaac tacctggtcc tcgacgtcga cgacatcccc    600
cgcgtcgtgc aggaggcctt cttcctcgca tcctctggtc gcccggggcc ggtgcttgtt    660
gacatcccca aggacatcca gcagcagatg gcggtgccgg cctgggacac gcccatgagt    720
ctgcctgggt acatcgcgcg ccttcccaag cctcccgcga ctgaatttct tgagcaggtg    780
ctgcgtcttg ttggtgaatc acggcgccct gttctttatg ttggcggtgg ctgtgcagta    840
tcaggtgagg agttgtgccg ctttgtggag ttgactggaa tcccagtcac aactactctt    900
atgggccttg gcaacttccc cagcgacgac ccactgtcac tgcgcatgct tggtatgcat    960
ggcacagtgt atgcaaatta tgcagtggat aaggccgatc tgttgcttgc atttggtgtg   1020
cggtttgatg atcgtgtgac agggaaaatt gaggcttttg caggcagagc taagattgtg   1080
cacattgata ttgatcctgc tgagattggc aagaacaagc agccacatgt gtccatctgt   1140
gcagatgtta agcttgcttt gcagggcatg aatactcttc tggaaggaag cacatcaaag   1200
aagagctttg acttcggctc atggcatgat gaattggatc agcaaaagag ggagtttccc   1260
cttgggtata aaatcttcaa tgaggaaatc cagccacaat atgctattca ggttcttgat   1320
gagttgacga aggggaaggc catcattgcc acaggtgttg ggcagcacca gatgtgggcg   1380
gcacagtatt acacttacaa gcggccaagg cagtggctgt cttcagctgg tcttggggct   1440
atgggatttg gtttgccggc tgctgctggt gctgctgtgg ccaacccagg tgtcactgtt   1500
gttgacatcg acggagatgg tagcttcctc atgaacattc aggagctagc tatgatccgt   1560
attgagaacc tcccagtcaa ggtctttgtg ctaaacaacc agcacctcgg gatggtggtg   1620
cagtgggagg acaggttcta taaggccaat agagcacaca cattcttggg aaacccagag   1680
aacgaaagtg agatatatcc agattttgtg gcaattgcca aagggttcaa cattccagca   1740
gtccgtgtga caaagaagag cgaagtccat gcagcaatca agaagatgct tgaggctcca   1800
gggccgtacc tcttggatat aatcgtcccg caccaggagc atgtgttgcc tatgatccct   1860
agtggtgggg ctttcaagga tatgatcctg gatggtgatg gcaggactgt gtattga      1917
```

<210> SEQ ID NO 34
<211> LENGTH: 2028
<212> TYPE: DNA
<213> ORGANISM: Artificial Sequence
<220> FEATURE:
<223> OTHER INFORMATION: ZmALS2 coding sequence

<400> SEQUENCE: 34

```
ctcccactcc gtgtccgtgg cacccacccc aaaccctcgc gccgcctccg agacagccgc     60
cgcaaccatg gccaccaccg ccgccgcgtc taccgcgctc actggcgcca ctaccgctgc    120
gcccaaggcg aggcgccggg cgcacctcct ggccacccgc cgcgccctcg ccgcgcccat    180
caggtgctca gcggcgtcac ccgccatgcc gatggctccc ccggccaccc cgctccggcc    240
gtggggcccc accgagcccc gcaagggtgc tgacatcctc gtcgagtccc tcgagcgctg    300
```

cggcgtccgc gacgtcttcg cctaccccgg cggcgcgtcc atggagatcc accaggcact 360
cacccgctcc cccgtcatcg ccaaccacct cttccgccac gagcaagggg aggcctttgc 420
cgcctccggc tacgcgcgct cctcgggccg cgtcggcgtc tgcatcgcca cctccggccc 480
cggcgccacc aacctagtct ccgcgctcgc cgacgcgctg ctcgattccg tccccatggt 540
cgccatcacg ggacaggtgc cgcgacgcat gattggcacc gacgccttcc aggagacgcc 600
catcgtcgag gtcacccgct ccatcaccaa gcacaactac ctggtcctcg acgtcgacga 660
catcccccgc gtcgtgcagg aggctttctt cctcgcctcc tctggtcgac cggggccggt 720
gcttgtcgac atccccaagg acatccagca gcagatggcg gtgcctgtct gggacaagcc 780
catgagtctg cctgggtaca ttgcgcgcct tcccaagccc cctgcgactg agttgcttga 840
gcaggtgctg cgtcttgttg gtgaatcccg gcgccctgtt ctttatgttg gcggtggctg 900
cgcagcatct ggtgaggagt tgcgacgctt tgtggagctg actggaatcc cggtcacaac 960
tactcttatg ggcctcggca acttccccag cgacgaccca ctgtctctgc gcatgcttgg 1020
tatgcatggc acggtgtatg caaattatgc agtggataag gccgatctgt tgcttgcatt 1080
tggtgtgcgg tttgatgatc gcgtgacagg gaagattgag gcttttgcaa gcagggctaa 1140
gattgtgcac gttgatattg atcccgctga gattggcaag aacaagcagc cacatgtgtc 1200
catctgtgca gatgttaagc ttgctttgca gggcatgaat gctcttcttg aaggaagcac 1260
atcaaagaag agctttgact ttggctcatg gaacgatgag ttggatcagc agaagaggga 1320 attcccccctt gggtataaaa catctaatga ggagatccag ccacaatatg ctattcaggt 1380
tcttgatgag ctgacgaaag gcgaggccat catcggcaca ggtgttgggc agcaccagat 1440
gtgggcggca cagtactaca cttacaagcg gccaaggcag tggttgtctt cagctggtct 1500
tggggctatg ggatttggtt tgccggctgc tgctggtgct tctgtggcca acccaggtgt 1560
cactgttgtt gacatcgatg gagatggtag ctttctcatg aacgttcagg agctagctat 1620
gatccgaatt gagaacctcc cggtgaaggt ctttgtgcta aacaaccagc acctggggat 1680
ggtggtgcag tgggaggaca ggttctataa ggccaacaga gcgcacacat acttgggaaa 1740
cccagagaat gaaagtgaga tatatccaga tttcgtgacg atcgccaaag ggttcaacat 1800
tccagcggtc cgtgtgacaa agaagaacga agtccgcgca gcgataaaga agatgctcga 1860
gactccaggg ccgtacctct tggatataat cgtcccacac caggagcatg tgttgcctat 1920
gatccctagt ggtggggctt tcaaggatat gatcctggat ggtgatggca ggactgtgta 1980
ctgatctaaa atccagcaag caactgatct aaaatccagc aagcaccg 2028

<210> SEQ ID NO 35
<211> LENGTH: 20
<212> TYPE: DNA
<213> ORGANISM: Artificial Sequence
<220> FEATURE:
<223> OTHER INFORMATION: ZmALS2_Ser621_for_spacer

<400> SEQUENCE: 35
ttgcctatga tccctagtgg 20

<210> SEQ ID NO 36
<211> LENGTH: 100
<212> TYPE: DNA
<213> ORGANISM: Artificial Sequence
<220> FEATURE:
<223> OTHER INFORMATION: gRNA_ZmALS2_Ser621_for

<400> SEQUENCE: 36
ttgcctatga tccctagtgg gttttagagc tagaaatagc aagttaaaat aaggctagtc 60
cgttatcaac ttgaaaaagt ggcaccgagt cggtgctttt 100

<210> SEQ ID NO 37
<211> LENGTH: 680
<212> TYPE: DNA
<213> ORGANISM: Artificial Sequence
<220> FEATURE:
<223> OTHER INFORMATION: ZmU6_gRNA_ZmALS2Ser621_for

<400> SEQUENCE: 37
ccttcttttg tttcacttat cagttttcac caagattgca tgccacttgg cgggttcatc 60
acgaagaacc ttccaataat gcaaaactgt ggacggacct ttttttaga ataatcgttc 120 taacaaaatt gcatagccct gtctgtctct tagttgatca tcagattggc cagtagcata 180
aactgaggta gccttggtcc atgcggcaaa aaaaaaagaa ccatctctct ctcttttgcc 240
agccaggtac actattgtgt tttacctctt ttttagtcta aaaaatactt gtcatttatt 300
ttctatccag ctgacaatct ttatggcccc tgacgaaata gttcgtggca aactggcaat 360
ggtcttttgc aaaacacgac gctgtgcacg tcagcacgtg agcttgcgat gtccactagg 420
gagctccatc cactgatcca cccccacgcg gcgtggcgtc gtcattaacg gcttgtgggg 480
aagggaacga gcaactaacc gataattagt accagaccgg ccagtgaacg atgccaaaac 540
cggcttataa gctcagctgc gacaaccgtt ttgttgccta tgatccctag tgggttttag 600
agctagaaat agcaagttaa aataaggcta gtccgttatc aacttgaaaa agtggcaccg 660
agtcggtgct ttttttttt 680

<210> SEQ ID NO 38
<211> LENGTH: 20
<212> TYPE: DNA
<213> ORGANISM: Artificial Sequence
<220> FEATURE:
<223> OTHER INFORMATION: ZmALS2_Ser621-del1_for_spacer

<400> SEQUENCE: 38
gttgcctatg atccctatgg 20

<210> SEQ ID NO 39
<211> LENGTH: 100
<212> TYPE: DNA
<213> ORGANISM: Artificial Sequence
<220> FEATURE:
<223> OTHER INFORMATION: gRNA_ZmALS2_Ser621-del1_for

<400> SEQUENCE: 39
gttgcctatg atccctatgg gttttagagc tagaaatagc aagttaaaat aaggctagtc 60
cgttatcaac ttgaaaaagt ggcaccgagt cggtgctttt 100

<210> SEQ ID NO 40
<211> LENGTH: 679
<212> TYPE: DNA
<213> ORGANISM: Artificial Sequence
<220> FEATURE:
<223> OTHER INFORMATION: ZmU6_gRNA_ZmALS2_Ser621del1_for

<400> SEQUENCE: 40
ccttcttttg tttcacttat cagttttcac caagattgca tgccacttgg cgggttcatc 60
acgaagaacc ttccaataat gcaaaactgt ggacggacct ttttttaga ataatcgttc 120 taacaaaatt gcatagccct gtctgtctct tagttgatca tcagattggc cagtagcata 180
aactgaggta gccttggtcc atgcggcaaa aaaaaaagaa ccatctctct ctcttttgcc 240
agccaggtac actattgtgt tttacctctt ttttagtcta aaaaatactt gtcatttatt 300
ttctatccag ctgacaatct ttatggcccc tgacgaaata gttcgtggca aactggcaat 360
ggtcttttgc aaaacacgac gctgtgcacg tcagcacgtg agcttgcgat gtccactagg 420
gagctccatc cactgatcca cccccacgcg gcgtggcgtc gtcattaacg gcttgtgggg 480
aagggaacga gcaactaacc gataattagt accagaccgg ccagtgaacg atgccaaaac 540
cggcttataa gctcagctgc gacaaccgtt ttgttgccta tgatccctat gggttttaga 600
gctagaaata gcaagttaaa ataaggctag tccgttatca acttgaaaaa gtggcaccga 660
gtcggtgctt tttttttt 679

<210> SEQ ID NO 41
<211> LENGTH: 25
<212> TYPE: DNA
<213> ORGANISM: Artificial Sequence
<220> FEATURE:
<223> OTHER INFORMATION: ZmALS_621_for

<400> SEQUENCE: 41
gaaagtgaga tatatccaga tttcg 25

<210> SEQ ID NO 42
<211> LENGTH: 24
<212> TYPE: DNA
<213> ORGANISM: Artificial Sequence
<220> FEATURE:
<223> OTHER INFORMATION: ZmALS_621_rev

<400> SEQUENCE: 42
tcagtacaca gtcctgccat cacc 24

<210> SEQ ID NO 43
<211> LENGTH: 30
<212> TYPE: DNA
<213> ORGANISM: Artificial Sequence
<220> FEATURE:
<223> OTHER INFORMATION: Wild-type ZmHRC region

<400> SEQUENCE: 43
gagcattctg actctgatga tgccaggaga 30

<210> SEQ ID NO 44
<211> LENGTH: 31
<212> TYPE: DNA
<213> ORGANISM: Artificial Sequence
<220> FEATURE:
<223> OTHER INFORMATION: ZmHRC_Asp94-ins1

<400> SEQUENCE: 44
gagcattctg actctgatga ttgccaggag a 31

<210> SEQ ID NO 45
<211> LENGTH: 29
<212> TYPE: DNA
<213> ORGANISM: Artificial Sequence
<220> FEATURE:
<223> OTHER INFORMATION: ZmHRC_Asp94-del1

<400> SEQUENCE: 45
gagcattctg actctgatga gccaggaga 29

<210> SEQ ID NO 46
<211> LENGTH: 27
<212> TYPE: DNA
<213> ORGANISM: Artificial Sequence
<220> FEATURE:
<223> OTHER INFORMATION: ZmHRC_Asp94-del3

<400> SEQUENCE: 46
gagcattctg actctgatgc caggaga 27

<210> SEQ ID NO 47
<211> LENGTH: 28
<212> TYPE: DNA
<213> ORGANISM: Artificial Sequence
<220> FEATURE:
<223> OTHER INFORMATION: ZmHRC_Asp94-del2

<400> SEQUENCE: 47
gagcattctg actctgatgg ccaggaga 28

<210> SEQ ID NO 48
<211> LENGTH: 24
<212> TYPE: DNA
<213> ORGANISM: Artificial Sequence
<220> FEATURE:
<223> OTHER INFORMATION: ZmHRC_Asp94-del6

<400> SEQUENCE: 48
gagcattctg actctgccag gaga 24

<210> SEQ ID NO 49
<211> LENGTH: 34
<212> TYPE: DNA
<213> ORGANISM: Artificial Sequence
<220> FEATURE:
<223> OTHER INFORMATION: ZmHRC_Asp94Phe

<400> SEQUENCE: 49
gagcattctg actctgattt tgccaggaga cgca 34

<210> SEQ ID NO 50
<211> LENGTH: 29
<212> TYPE: DNA
<213> ORGANISM: Artificial Sequence
<220> FEATURE:
<223> OTHER INFORMATION: Wild-type Lox1 region

<400> SEQUENCE: 50
cacctacgtc gacaccaccc ccggcgagt 29

<210> SEQ ID NO 51
<211> LENGTH: 30
<212> TYPE: DNA
<213> ORGANISM: Artificial Sequence
<220> FEATURE:
<223> OTHER INFORMATION: TaLox1_Val286-ins1

<400> SEQUENCE: 51
cacctacgat cgacaccacc cccggcgagt 30

<210> SEQ ID NO 52
<211> LENGTH: 26
<212> TYPE: DNA
<213> ORGANISM: Artificial Sequence
<220> FEATURE:
<223> OTHER INFORMATION: TaLox1_Val286-del3

<400> SEQUENCE: 52
cacctacgac accacccccg gcgagt 26

<210> SEQ ID NO 53
<211> LENGTH: 27
<212> TYPE: DNA
<213> ORGANISM: Artificial Sequence
<220> FEATURE:
<223> OTHER INFORMATION: TaLox1_Val286-del2

<400> SEQUENCE: 53
cacctacgga caccaccccc ggcgagt 27

<210> SEQ ID NO 54
<211> LENGTH: 24
<212> TYPE: DNA
<213> ORGANISM: Artificial Sequence
<220> FEATURE:
<223> OTHER INFORMATION: TaLox1_Val286-del5

<400> SEQUENCE: 54
cacctacgac cacccccggc gagt 24

<210> SEQ ID NO 55
<211> LENGTH: 28
<212> TYPE: DNA
<213> ORGANISM: Artificial Sequence
<220> FEATURE:
<223> OTHER INFORMATION: TaLox1_Val286-del1

<400> SEQUENCE: 55
cacctacgcg acaccacccc cggcgagt 28

<210> SEQ ID NO 56
<211> LENGTH: 26
<212> TYPE: DNA
<213> ORGANISM: Artificial Sequence
<220> FEATURE:
<223> OTHER INFORMATION: TaLox1_Val286Glu

<400> SEQUENCE: 56
cacctacgaa gacacccccg gcgagt 26

<210> SEQ ID NO 57
<211> LENGTH: 34
<212> TYPE: DNA
<213> ORGANISM: Artificial Sequence
<220> FEATURE:
<223> OTHER INFORMATION: ZmALS2_Ser621Asn

<400> SEQUENCE: 57
atgtgttgcc tatgatccct aatggtgggg cttt 34

<210> SEQ ID NO 58
<211> LENGTH: 34
<212> TYPE: DNA
<213> ORGANISM: Artificial Sequence
<220> FEATURE:
<223> OTHER INFORMATION: Synthetic

<400> SEQUENCE: 58
gagcattctg actctgatga tgccaggaga cgca 34

<210> SEQ ID NO 59
<211> LENGTH: 28
<212> TYPE: DNA
<213> ORGANISM: Artificial Sequence
<220> FEATURE:
<223> OTHER INFORMATION: Synthetic

<400> SEQUENCE: 59
gcattctgac tctgatgatg ccaggaga 28

<210> SEQ ID NO 60
<211> LENGTH: 31
<212> TYPE: DNA
<213> ORGANISM: Artificial Sequence
<220> FEATURE:
<223> OTHER INFORMATION: Synthetic

<400> SEQUENCE: 60
gagcattctg actctgatga ttgccaggag a 31

<210> SEQ ID NO 61
<211> LENGTH: 29
<212> TYPE: DNA
<213> ORGANISM: Artificial Sequence
<220> FEATURE:
<223> OTHER INFORMATION: Synthetic

<400> SEQUENCE: 61
gagcattctg actctgatga gccaggaga 29

<210> SEQ ID NO 62
<211> LENGTH: 27
<212> TYPE: DNA
<213> ORGANISM: Artificial Sequence
<220> FEATURE:
<223> OTHER INFORMATION: Synthetic

<400> SEQUENCE: 62
gagcattctg actctgatgc caggaga 27

<210> SEQ ID NO 63
<211> LENGTH: 28
<212> TYPE: DNA
<213> ORGANISM: Artificial Sequence
<220> FEATURE:
<223> OTHER INFORMATION: Synthetic

<400> SEQUENCE: 63
gagcattctg actctgatgg ccaggaga 28

<210> SEQ ID NO 64
<211> LENGTH: 24
<212> TYPE: DNA
<213> ORGANISM: Artificial Sequence
<220> FEATURE:
<223> OTHER INFORMATION: Synthetic

<400> SEQUENCE: 64
gagcattctg actctgccag gaga 24

<210> SEQ ID NO 65
<211> LENGTH: 31
<212> TYPE: DNA
<213> ORGANISM: Artificial Sequence
<220> FEATURE:
<223> OTHER INFORMATION: Synthetic

<400> SEQUENCE: 65
gagcattctg actctgatgc caggagacgc a 31

<210> SEQ ID NO 66
<211> LENGTH: 32
<212> TYPE: DNA
<213> ORGANISM: Artificial Sequence
<220> FEATURE:
<223> OTHER INFORMATION: Synthetic

<400> SEQUENCE: 66
gagcattctg actctgattg ccaggagacg ca 32

<210> SEQ ID NO 67
<211> LENGTH: 33
<212> TYPE: DNA
<213> ORGANISM: Artificial Sequence
<220> FEATURE:
<223> OTHER INFORMATION: Synthetic

<400> SEQUENCE: 67
gagcattctg actctgattt gccaggagac gca 33

<210> SEQ ID NO 68
<211> LENGTH: 34
<212> TYPE: DNA
<213> ORGANISM: Artificial Sequence
<220> FEATURE:
<223> OTHER INFORMATION: Synthetic

<400> SEQUENCE: 68
gagcattctg actctgattt tgccaggaga cgca 34

<210> SEQ ID NO 69
<211> LENGTH: 26
<212> TYPE: DNA
<213> ORGANISM: Artificial Sequence
<220> FEATURE:
<223> OTHER INFORMATION: Synthetic

<400> SEQUENCE: 69
cacctacgtc gacacccccg gcgagt 26

<210> SEQ ID NO 70
<211> LENGTH: 26
<212> TYPE: DNA
<213> ORGANISM: Artificial Sequence
<220> FEATURE:
<223> OTHER INFORMATION: Synthetic

<400> SEQUENCE: 70
gtggatgcag ctgtgggggc cgctca 26

<210> SEQ ID NO 71
<211> LENGTH: 17
<212> TYPE: DNA
<213> ORGANISM: Artificial Sequence
<220> FEATURE:
<223> OTHER INFORMATION: Synthetic

<400> SEQUENCE: 71
tgcagctgtg ggggccg 17

<210> SEQ ID NO 72

<211> LENGTH: 28
<212> TYPE: DNA
<213> ORGANISM: Artificial Sequence
<220> FEATURE:
<223> OTHER INFORMATION: Synthetic

<400> SEQUENCE: 72
cacctacgtc gacaccaccc ccggcagt 28

<210> SEQ ID NO 73
<211> LENGTH: 30
<212> TYPE: DNA
<213> ORGANISM: Artificial Sequence
<220> FEATURE:
<223> OTHER INFORMATION: Synthetic

<400> SEQUENCE: 73
cacctacgat cgacaccacc cccggcgagt 30

<210> SEQ ID NO 74
<211> LENGTH: 26
<212> TYPE: DNA
<213> ORGANISM: Artificial Sequence
<220> FEATURE:
<223> OTHER INFORMATION: Synthetic

<400> SEQUENCE: 74
cacctacgac accaccccg gcgagt 26

<210> SEQ ID NO 75
<211> LENGTH: 27
<212> TYPE: DNA
<213> ORGANISM: Artificial Sequence
<220> FEATURE:
<223> OTHER INFORMATION: Synthetic

<400> SEQUENCE: 75
cacctacgga caccaccccc ggcgagt 27

<210> SEQ ID NO 76
<211> LENGTH: 24
<212> TYPE: DNA
<213> ORGANISM: Artificial Sequence
<220> FEATURE:
<223> OTHER INFORMATION: Synthetic

<400> SEQUENCE: 76
cacctacgac cacccccggc gagt 24

<210> SEQ ID NO 77
<211> LENGTH: 28
<212> TYPE: DNA
<213> ORGANISM: Artificial Sequence
<220> FEATURE:
<223> OTHER INFORMATION: Synthetic

<400> SEQUENCE: 77
cacctacgcg acaccacccc cggcgagt 28

<210> SEQ ID NO 78
<211> LENGTH: 24
<212> TYPE: DNA
<213> ORGANISM: Artificial Sequence
<220> FEATURE:
<223> OTHER INFORMATION: Synthetic

<400> SEQUENCE: 78
cacctacgga cacccccggc gagt 24

<210> SEQ ID NO 79
<211> LENGTH: 24
<212> TYPE: DNA
<213> ORGANISM: Artificial Sequence
<220> FEATURE:
<223> OTHER INFORMATION: Synthetic

<400> SEQUENCE: 79
gtggatgcct gtgggggccg ctca 24

<210> SEQ ID NO 80
<211> LENGTH: 25
<212> TYPE: DNA
<213> ORGANISM: Artificial Sequence
<220> FEATURE:
<223> OTHER INFORMATION: Synthetic

<400> SEQUENCE: 80
cacctacgag acacccccgg cgagt 25

<210> SEQ ID NO 81
<211> LENGTH: 25
<212> TYPE: DNA
<213> ORGANISM: Artificial Sequence
<220> FEATURE:
<223> OTHER INFORMATION: Synthetic

<400> SEQUENCE: 81
gtggatgctc tgtgggggcc gctca 25

<210> SEQ ID NO 82
<211> LENGTH: 26
<212> TYPE: DNA
<213> ORGANISM: Artificial Sequence
<220> FEATURE:
<223> OTHER INFORMATION: Synthetic

<400> SEQUENCE: 82
cacctacgaa gacacccccg gcgagt 26

<210> SEQ ID NO 83
<211> LENGTH: 26
<212> TYPE: DNA
<213> ORGANISM: Artificial Sequence
<220> FEATURE:
<223> OTHER INFORMATION: Synthetic

<400> SEQUENCE: 83
gtggatgctt ctgtgggggc cgctca 26

<210> SEQ ID NO 84
<211> LENGTH: 34
<212> TYPE: DNA
<213> ORGANISM: Artificial Sequence
<220> FEATURE:
<223> OTHER INFORMATION: Synthetic

<400> SEQUENCE: 84
atgtgttgcc tatgatccct agtggtgggg cttt 34

<210> SEQ ID NO 85
<211> LENGTH: 33
<212> TYPE: DNA

-continued

```
<213> ORGANISM: Artificial Sequence
<220> FEATURE:
<223> OTHER INFORMATION: Synthetic

<400> SEQUENCE: 85

atgtgttgcc tatgatccct atggtggggc ttt                          33


<210> SEQ ID NO 86
<211> LENGTH: 34
<212> TYPE: DNA
<213> ORGANISM: Artificial Sequence
<220> FEATURE:
<223> OTHER INFORMATION: Synthetic

<400> SEQUENCE: 86

atgtgttgcc tatgatccct aatggtgggg cttt                         34
```